United States Patent
Anantaneni et al.

(10) Patent No.: US 6,630,430 B1
(45) Date of Patent: Oct. 7, 2003

(54) FUEL AND OIL DETERGENTS

(75) Inventors: Prakasa R. Anantaneni, Austin, TX (US); George A. Smith, Austin, TX (US)

(73) Assignee: Huntsman Petrochemical Corporation, Austin, TX (US)

(*) Notice: Subject to any disclaimer, the term of this patent is extended or adjusted under 35 U.S.C. 154(b) by 291 days.

(21) Appl. No.: 09/616,568

(22) Filed: Jul. 14, 2000

Related U.S. Application Data

(60) Continuation-in-part of application No. 09/559,841, filed on Apr. 26, 2000, now Pat. No. 6,562,776, and a continuation-in-part of application No. 08/598,692, filed on Feb. 8, 1996, now Pat. No. 5,847,254, and a continuation-in-part of application No. 09/174,891, filed on Oct. 19, 1998, now Pat. No. 6,133,492, and a continuation-in-part of application No. 08/879,745, filed on Jun. 20, 1997, now Pat. No. 6,315,964, which is a division of application No. 08/598,695, filed on Feb. 8, 1996, now Pat. No. 5,770,782.

(60) Provisional application No. 60/178,823, filed on Jan. 28, 2000.

(51) Int. Cl.⁷ .................................................. C10M 0/00
(52) U.S. Cl. ................... 508/413; 508/389; 508/390; 508/391; 184/1.5; 252/70
(58) Field of Search .................. 508/413, 389, 508/390, 391; 184/1.5; 252/70

(56) References Cited

U.S. PATENT DOCUMENTS

| | | | |
|---|---|---|---|
| 3,342,888 A | 9/1967 | DeWitt et al. ............... 260/671 |
| 3,387,056 A | 6/1968 | McEwan et al. ............. 260/671 |
| 3,478,118 A | 11/1969 | Sorgenti ..................... 260/671 |
| 3,509,225 A | 4/1970 | Wotring et al. ............. 260/671 |
| 3,631,123 A | 12/1971 | Becker ................... 260/674 A |
| 4,072,730 A | 2/1978 | Winter, III ............. 260/671 R |
| 4,162,236 A | 7/1979 | Feierstein et al. .......... 252/558 |
| 4,180,691 A | 12/1979 | Illingworth ................. 585/455 |
| 4,301,316 A | 11/1981 | Young ........................ 585/455 |
| 4,301,317 A | 11/1981 | Young ........................ 585/455 |
| 4,467,128 A | 8/1984 | Vora ........................... 585/456 |
| 4,503,277 A | 3/1985 | Himes ........................ 585/455 |
| 4,537,709 A | 8/1985 | Edge et al. ................. 252/558 |
| 4,767,551 A * | 8/1988 | Hunt et al. ................. 252/32.7 |
| 4,783,567 A | 11/1988 | Kocal ......................... 585/464 |
| 4,891,466 A | 1/1990 | Kocal ......................... 585/464 |
| 4,948,521 A * | 8/1990 | Stewart, Jr. et al. .......... 252/28 |
| 4,962,256 A | 10/1990 | Le et al. ..................... 585/467 |
| 5,012,021 A | 4/1991 | Vora et al. .................. 585/315 |
| 5,196,574 A | 3/1993 | Kocal ........................... 562/94 |
| 5,302,732 A | 4/1994 | Steigleder et al. ............ 554/98 |
| 5,344,997 A | 9/1994 | Kocal ......................... 568/628 |
| 5,574,198 A | 11/1996 | Radici et al. ............... 585/323 |
| 5,741,763 A * | 4/1998 | Matsushita ................. 508/413 |
| 5,792,732 A * | 8/1998 | Jao et al. .................... 508/391 |
| 6,342,473 B1 | 1/2002 | Kott et al. ................... 510/357 |

FOREIGN PATENT DOCUMENTS

| | | |
|---|---|---|
| EP | 353 813 | 2/1990 |
| WO | WO 99/05243 | 2/1999 |
| WO | WO 00/23548 | 4/2000 |
| WO | WO 00/23549 | 4/2000 |

OTHER PUBLICATIONS

"Linear Alkylbenzene" by DeAlmeida et al. JAOCS, vol. 71, No. 7 (Jul., 1994).

* cited by examiner

*Primary Examiner*—Yogendra N. Gupta
*Assistant Examiner*—D. G. Hamlin
(74) *Attorney, Agent, or Firm*—Christopher J. Whewell

(57) ABSTRACT

This invention is directed to lubricating compositions which contain detergent components derived from linear alkylbenzenes including sulfonates and salts and esters thereof. Detergents provided by the invention have a higher content of the 2-phenyl alkylbenzene isomers than was previously available in materials of prior art. The detergents of the present invention are more powerful detergents over those previously available and may be employed as additives in various lubricating compositions, including motor oils, cutting fluids, emulsions, and motor fuels.

40 Claims, 3 Drawing Sheets

FUEL AND OIL DETERGENTS

This application is a continuation-in-part application of application Ser. Nos.: 09/559,841 filed Apr. 26, 2000 U.S. Pat. No. 6,562,776; 08/598,692, filed Feb. 8, 1996 U.S. Pat. No. 5,847,254; and 09/174,891 filed Oct. 19, 1998 U.S. Pat. No. 6,133,492 and of application Ser. No. 08/879,745, filed Jun. 20, 1997 U.S. Pat. No. 6,315,964 which is a divisional of Ser. No. 08/598,695, filed Feb. 8, 1996, now U.S. Pat. No. 5,770,782, the contents of which are expressly incorporated herein by reference. This Application claims the benefit of U. S. Provisional Application No. 60/178,823 filed Jan. 28, 2000, which is currently still pending.

This invention relates to a oil-soluble compositions of matter useful as detergent components in hydrocarbon oils useful for a wide range of purposes, including without limitation general lubricants, lubricating oils for internal combustion engines, cutting fluids, emulsions, and dispersions.

More particularly, the invention relates to oil-soluble linear alkylbenzenes comprising alkyl chains having between about 18 and 30 carbon atoms in which the alkylbenzenes have a low dialkylate content and unique isomer distribution, including their sulfonate and other water soluble and solubilizable derivatives.

BACKGROUND

The chemical structure and use of linear alkylbenzenes and their derivatives, including their sulfonate derivatives, in the manufacture of detergents is well known. Generally, linear alkylbenzenes are produced by an alkylation reaction (according to one of any well known processes for producing such materials) in which the net result is the appendage of a hydrocarbyl radical to a benzene ring. The source of the hydrocarbyl radical may be a branched or a linear olefin, either an internal olefin or an alpha olefin, and in practice a mixture of linear olefins is typically used, which mixture comprises various olefins having different numbers of carbon atoms per molecule. For the manufacture of detergents, the range of carbon numbers (the number of carbon atoms per molecule of an olefin used) of an olefin mixture used in the alkylation reaction is typically in the range of between about 8 and 15 (inclusive) carbon atoms per molecule, which molecules are sometimes collectively referred to by those in the art as the "detergent range".

Alkylation of benzene using olefins in the detergent range leads to a reaction product mixture which contains alkylated benzenes having hydrocarbyl radicals of different chain length appended to a benzene ring, and also contains position isomers of these alkylation products. Thus, a reaction mixture from the alkylation of benzene using detergent range olefins is often complex in makeup.

Of the possible position isomers referred to above, it has been recently discovered that detergents prepared from alkylbenzenes having the benzene ring located at the 2-position on the hydrocarbyl radical possess enhanced detergency and other beneficial properties over the other isomers produced in the alkylation. This is believed in part to be true because the hydrocarbon chain that is appended to the ring extends a greater distance in space in isomers having a phenyl group in the 2-position than the other position isomers, thus providing a molecule having a more volumetrically exposed hydrocarbon chain portion over other position isomers. Among other things, this increased exposure provides increased availability for interaction with hydrophobic materials which are sought to be solubilized in an aqueous medium, when the alkylbenzene also includes a hydrophilic moiety, such as a sulfonate group bonded to the benzene ring.

Surprisingly, more than one source of information in the prior art mentions that a high 2-phenyl isomer content in alkylbenzenes-derived detergent materials is undesirable. For example, U.S. Pat. No. 3,342,888 mentions at column 2, line 37 et seq. that a high 2-phenyl isomer content is associated with poor sudsing characteristics. U.S. Pat. No. 3,387,056 mentions at column 2, lines 21–24 that a lower 2-phenyl isomer content improves the product. U.S. Pat. No. 3,509,225 mentions at column 1, lines 59–62 that the 2-phenyl isomer is objectionable for use in commercial detergent products because of its relatively low water solubility. However, quite the opposite has been found to be true for the compositions according to this invention, and it has now been deemed desirable to provide alkylbenzenes having extremely high amounts of the 2-phenyl isomer alkylation reaction products.

Detergents useful as components in hydrocarbon oils are often possessive in general of the same properties as detergents useful in aqueous media, that is, their molecules contain both a hydrophilic and a hydrophobic portion. However, in many applications it may be beneficial to employ alkylbenzenes having longer hydrocarbon chains on the benzene ring than those found in conventional detergents, for example to enhance solubility in hydrocarbon oils, or to provide increased compatibility and chemical inertness with respect to other components of the formulation, depending upon the intended use. The production of sulfonates by reaction with, e.g., $SO_3$, is well known to those skilled in the art. See, for example, the article "Sulfonates" in Kirk-Othmer "Encyclopedia of Chemical Technology", Second Edition, Vol. 19, pp. 291 et seq. published by John Wiley & Sons, N.Y. (1969). Other descriptions of neutral and basic sulfonate salts and techniques for making them can be found in the following U.S. Pat. Nos. 2,174,110; 2,174,506; 2,174,508; 2,193,824; 2,197,800; 2,202,781; 2,212,786; 2,213,360; 2,228,598; 2,223,676; 2,239,974; 2,263,312; 2,276,090; 2,276,097; 2,315,514; 2,319,121; 2,321,022; 2,333,568; 2,333,788; 2,335,259; 2,337,552; 2,347,568; 2,366,027; 2,374,193; 2,383,319; 3; 312,618; 3,471,403; 3,488,284; 3,595,790; and 3,798,012. These and all other patents, books, excerpts, articles, and literature cited herein are hereby incorporated by reference for their disclosures.

Although the prior art is replete with prior art concerning the use of alkylbenzene based detergents in hydrocarbon based oils such as motor oils, hydraulic fluids, cutting fluids, etc., none have thus far provided commercially quantities of an alkylbenzene based detergent component in which the hydrocarbon tails of the molecule have carbon numbers of any integral value in the range of between about 16 and 30 carbon atoms per molecule, in which the 2-phenyl isomer content is greater than about 50%, at prices low enough to render such materials economically viable from the end user perspective. Thus I have recognized that a need exists for a method of linear alkylbenzene ("LAB") production having high substrate olefin conversion, high selectivity to 2-phenyl isomer LAB, and employing a catalyst having long lifetimes and easy handling, by which high 2-phenyl isomer content and low dialkylate content can be achieved in materials having relatively long hydrocarbon tails attached to a benzene ring in a linear alkylbenzene based detergent.

The present invention employs a mordenite catalyst in the production of long-tail linear alkylbenzenes. The particular mordenites useful in this invention may in one form of the invention be mixed with a different catalyst that does not afford high 2-phenyl isomer LAB production, to provide essentially any desired percentage content of 2-phenyl isomer in the range of about 20–82% (on a weight basis) in the finished product by adjusting the amounts of each catalyst. In this way, LAB may be produced having a higher 2-phenyl isomer content than would be produced using the non-mordenite catalyst of this invention.

Thus, in one broad respect, this invention is a process for the production of linear alkylbenzenes which comprises contacting benzene and an olefin having about 8 to about 30 carbons in the presence of a mixed catalyst bed to form linear alkylbenzenes, wherein the mixed catalyst bed comprises fluorine-containing mordenite and a second, solid linear alkylbenzene alkylation catalyst, wherein the second alkylation catalyst has a selectivity to the 2-phenyl isomer of the linear alkylbenzenes less than the selectivity of the fluorine-containing mordenite.

In another broad respect, this invention is a process for the production of linear alkylbenzenes, comprising:

dehydrogenating a paraffin to form an olefin;

sending a feed stream of benzene and the olefin through a conduit to a linear alkylbenzenes alkylation reactor containing a fluorine-containing mordenite and a second alkylation catalyst, wherein the second alkylation catalyst has a selectivity to the 2-phenyl isomer of the linear alkylbenzenes less than the selectivity of the fluorine-containing mordenite;

reacting the benzene and olefin in the reactor to form a crude linear alkylbenzenes stream;

distilling the crude linear alkylbenzenes stream in a first distillation column to separate benzene that did not react and to form a benzene-free linear alkylbenzenes stream;

distilling the benzene-free linear alkylbenzenes stream in a second distillation column to separate any paraffin present and to form a paraffin-free linear alkylbenzenes stream;

distilling the paraffin-free linear alkylbenzene stream in a third distillation column to provide an overhead of a purified linear alkylbenzene stream and removing a bottoms stream containing heavies.

This invention, in another broad respect, is a process useful for the production of monoalkylated benzenes, comprising contacting benzene with an olefin or a mixture of olefins that contains or containing from about 8 to about 30 carbons in the presence of fluorine-containing mordenite under conditions such that linear monoalkylated benzene is formed.

In a second broad respect, this invention is a process useful for the production of monoalkylated benzenes, comprising introducing a feed comprising olefin having about 16 to about 30 carbons and benzene into a fluorine-containing mordenite catalyst bed under conditions such that monoalkylated benzene is produced, allowing benzene, olefin, and monoalkylated benzene to descend (fall) into a reboiler from the catalyst bed, removing monoalkylated benzene from the reboiler, and heating the contents of the reboiler such that benzene refluxes to further contact the fluorine-containing mordenite.

In another broad aspect, this invention relates to mordenite useful for alkylating benzene having a silica to alumina molar ratio of about 10:1 to about 100:1; wherein the mordenite has been treated with an aqueous hydrogen fluoride solution such that the mordenite contains from about 0.1 to about 4 percent fluorine by weight.

In another broad respect, this invention is a method useful for the preparation of fluorine-containing mordenite, comprising contacting a mordenite having a silica to alumina molar ratio in a range from about 10:1 to about 100:1 with an aqueous hydrogen fluoride solution having a concentration of hydrogen fluoride in the range of from about 0.1 to about 10 percent by weight such that the mordenite containing fluorine is produced, collecting the fluorine-containing mordenite by filtration, and drying.

The fluorine treated mordenite catalyst advantageously produces high selectivities to the 2-phenyl isomer in the preparation of LAB, generally producing selectivities of about 70 percent or more. Also, the fluorine treated mordenite enjoys a long lifetime, preferably experiencing only a 25 percent or less decrease in activity after 400 hours on stream. A process operated in accordance with the apparatus depicted in FIGS. 1 and 2 has the advantage that rising benzene from the reboiler continuously cleans the catalyst to thereby increase lifetime of the catalyst. In addition, this invention advantageously produces little or no dialkylated benzene, which is not particularly as useful for detergent manufacture, as well as little or no tetralin derivatives.

Certain terms and phrases have the following meanings as used herein.

"Meq/g" means milliequivalents of titratable acid per gram of catalyst, which is a unit used to describe acidity of the catalysts. Acidity is generally determined by titration with a base, as by adding excessive base, such as sodium hydroxide, to the catalyst and then back titrating the catalyst.

"Conv." and "Conversion" mean the mole percentage of a given reactant converted to product. Generally, olefin conversion is about 95 percent or more in the practice of this invention.

"Sel." and "Selectivity" mean the mole percentage of a particular component in the product. Generally, selectivity to the 2-phenyl isomer is about 70% or more in the practice of this invention.

"LAB" means a mixture linear alkylbenzenes which comprises a benzene ring appended to any carbon atom of a substantially linear alkyl chain having any number of carbon atoms in the range of 18 to 30, inclusive. The mordenite catalyst of the present invention is useful as a catalyst useful in the production of LAB's in accordance with the process of manufacturing LAB's of this invention. LAB is useful as starting material to produce sulfonated LAB, which itself is useful as a surfactant.

"LAB sulfonates" means LAB which has been sulfonated to include an acidic sulfonate group appended to the benzene ring (thus forming a "parent acid"), and subsequently rendered to a form more soluble to aqueous solution than the parent acid by neutralization using any of alkali metal hydroxides, alkaline earth hydroxides, ammonium hydroxides, alkylammonium hydroxides, or any chemical agent known by those skilled in the art to react with linear alkylbenzene sulfonic acids to form water-soluble LAB sulfonates.

"Detergent range" means an olefin, alkyl group, or molecular species (including without limitation LAB and LAB sulfonates) that comprises any number of carbon atoms selected from:16, 17, 18, 19, 20, 21, 22, 23, 24, 25, 26, 27, 28, 29, or 30, as warranted by the context.

"Substantially linear" when referring to a hydrocarbon or alkyl chain that is part of an alkylbenzene, whether the alkylbenzene is sulfonated or not, means a hydrocarbon comprising between 16 and 30 carbon atoms linked to one another to form a straight chain, wherein the carbon atoms of said straight chain may have only hydrogen atoms or a methyl group bonded to them as appendages.

"Branched alkyl" when referring to a hydrocarbon or alkyl chain that is part of an alkylbenzene, whether the alkylbenzene is sulfonated or not, means a hydrocarbon comprising between 16 and 30 carbon atoms linked to one another to form a straight chain, wherein one or more of the carbon atoms of said straight chain may have a hydrogen atom and any alkyl group other than a methyl group (including without limitation ethyl groups), bonded to them as appendages.

"Branched alkylbenzene" means a molecular species which comprises a branched alkyl chain appended to a benzene ring.

"Branched alkylbenzene sulfonate" means a water-soluble salt of a branched alkylbenzene that has been sulfonated.

"2-phenyl alkylbenzenes" means a benzene ring having at least one alkyl group attached to it, wherein the alkyl group comprises any number of carbon atoms between 16 and 30 (including every integral number therebetween) linked to one another so as to form a substantially linear chain and wherein the benzene ring is attached the alkyl group at a carbon atom that is adjacent to the terminal carbon of the substantially linear chain. Thus, the carbon atom that is attached to the benzene ring has a methyl group and an alkyl group attached to it in a 2-phenyl alkylbenzene. Thus, the 2-phenyl isomer of the LAB produced in accordance with this invention is of the formula:

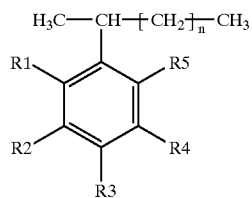

in which n is from about 13 to about 28 and preferably from about 16 to about 24, and in which $R_1$, $R_2$, $R_3$, R4, and $R_5$ are each independently selected from the group consisting of: hydrogen, methyl, ethyl, propyl, and butyl.

"Sulfonated 2-phenyl alkylbenzenes" means 2-phenyl alkylbenzenes as defined above which further comprise a sulfonate group attached to the benzene ring of a 2-phenyl alkylbenzene, regardless of the position of the sulfonate group on the ring with respect to the location of the alkyl group. However, it is typical, though not always the case for the sulfonate group to appear in the position $R_3$ above with respect to a single alkyl group attached to the benzene ring, as shown in the following structure:

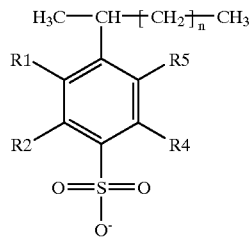

"Motor fuel" means those compositions generally recognized by those in the art as liquid hydrocarbon fuels in the gasoline boiling range, including hydrocarbon base fuels. Within the meaning of this term is included those fuels often termed as "petroleum distillate fuels" by those in the art and which have the above characteristic boiling points. The term is, however, not intended to be restricted to straight-run distillate fractions. The distillate fuel can be straight-run distillate fuel, catalytically or thermally cracked (including hydrocracked) distillate fuel, or a mixture of straight-run distillate fuel, naphthas and the like with cracked distillate stocks. Also, the base fuels used in the formulations of the fuel compositions of the present invention can be treated in accordance with well-known commercial methods such as acid or caustic treatments, hydrogen solvent refining, clay treatment, etc. Gasolines are supplied in a number of different grades depending upon the type of service for which they are intended. The gasolines useful in the present invention include those designed as motor and aviation gasolines. Motor gasolines include those defined by ASTM specification D-439-73 and are composed of a mixture of various types of hydrocarbons including aromatics, olefins, paraffins, isoparaffins, naphthalenes, and occasionally diolefins. Motor gasolines normally have a boiling range within the limits of about 20 degrees C. to about 230 degrees C., while aviation gasolines have narrower boiling ranges, usually within the limits of about 37 degrees C. to 165 degrees C. Also within this definition are the kerosene range fuels, which include diesel fuels and jet fuel.

"Ashless Dispersants" means any material regarded by those in the motor fuel arts as possessive of dispersant characteristics and which upon combustion leaves substantially no ash.

In this specification and the appended claims, all parts and percentages are expressed in terms of weight percent, unless specified otherwise.

DETAILED DESCRIPTION

Figure 1:
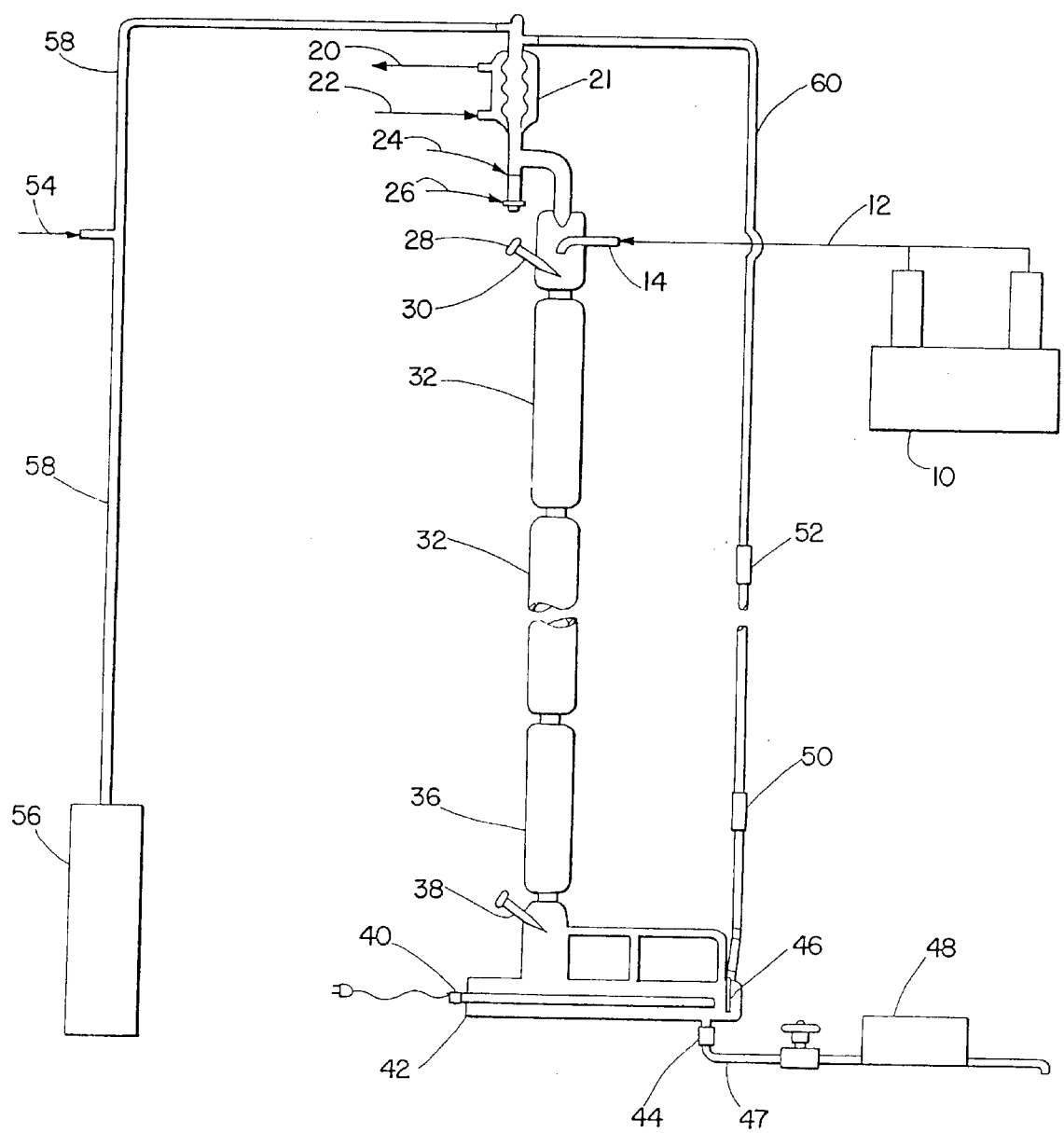
FIG. 1 shows a representation of a first continuous reactive distillation column employed in the practice of this invention.

The catalysts of this invention are fluorine-containing mordenites, which is a form of zeolite. A catalyst according to this invention is prepared from a hydrogen mordenite (typically having 0.1 percent or less of sodium) having a silica-alumina molar ratio of from about 10:1 to about 100:1. More typically, the starting mordenite has a silica/alumina molar ratio of from about 10:1 to about 50:1. The starting hydrogen mordenite, which is commercially, available, is treated with an aqueous solution of hydrogen fluoride ("HF") to produce the active, highly selective catalyst of the invention. In the course of such HF treatment, as well as during subsequent calcination of said HF-treated mordenite, the silica/alumina molar ratio typically increases. Finished catalysts prepared in accordance with the principles of this invention may have a fluorine content of from about 0.1 to about 4 percent by weight, including every hundredth percentage therebetween, but preferably contain about 1 percent fluorine by weight based upon the total weight of the finished catalyst.

The aqueous solution used to treat the mordenite may contain a range of HF concentrations. Generally, the HF concentration is a minimum of about 0.1 percent by weight. Below such minimum concentration, the effect of the fluorine treatment significantly decreases, resulting in the undesirable need for repeated treatments. However, repeated treatments do ultimately provide a catalyst material useful according to the invention, and in such regard these materials are properly considered to be functional equivalents of other catalysts prepared in accordance with the invention. Generally, the maximum level of HF in a treating solution intended to be used for treating a mordenite to provide a catalyst according to a preferred form of the invention is about 10 percent by weight. Above a concentration of about 10 percent by weight, the HF-bearing treating solution begins to alter the crystallinity of the mordenite, and may adversely affect its catalytic properties.

The aqueous HF solution may be prepared by simple dilution of commercially available aqueous stock solutions of HF, such as 48% HF solutions, to a desired concentration. Alternatively, it is possible to sparge gaseous HF into water to provide an aqueous HF solution.

Typically, the treatment with aqueous hydrogen fluoride solution is carried out by adding mordenite powder, pellets, or extrudates to an aqueous HF solution at a temperature of from about 0° C. to about 50° C. using agitation and an addition rate sufficient to prevent lumping of the mordenite, and spattering of the solution. The agitation of the HF solution to which the mordenite has been added is continued for a time sufficient to achieve the desired level of fluorine in the mordenite. This time may vary, as is known by those skilled in the art, being dependent on the agitation, temperature, the amount of HF available, which depends upon the concentration of the HF solution and the relative amount of HF solution to the amount of mordenite being treated. After treatment, the mordenite can be recovered by filtration, and then dried. It is also possible to impregnate the mordenite to incipient wetness with a given HF solution, as well as to treat the mordenite with gaseous hydrogen fluoride. Preferably the fluoride-treated mordenite is calcined in air prior to its being used in the alkylation process. The preferred calcination temperature is any degree of temperature in the range from about 400° C. to about 600° C. Mordenite may alternatively be fluorinated using other materials such as ammonium fluoride, fluosilicic acid, fluorided silicon compounds, fluorided hydrocarbons, or any compound capable of losing a fluorine atom to a mordenite when brought into contact with the mordenite.

The mordenite can be used in the practice of this invention as a powder, in pellet form, as granules, or as extrudates. The mordenite may be formed into pellets or extrudates using binders and techniques well known to those of skill in the art, such as alumina, silica or mixtures thereof. Catalysts according to the invention may also be supported on an inert carrier, such as alumina or silica, as the preparation of supported catalysts is well known in the art.

Reactants for LAB Production

In the practice of this invention, benzene or a substituted benzene such as toluene, ethylbenzene, propylbenzene, butylbenzene, or one or more xylenes is alkylated with an olefinic material to form LAB. Olefins and benzene can be handled and purified using standard techniques recognized by those of ordinary skill in the art. In this regard, it is preferred that the reactants are substantially free from water and alcohol, as the presence of hydroxy groups tends to hinder the reaction, possibly by poisoning the catalyst. The olefins employed in the practice of this invention have from about 16 to about 30 carbons per molecule, and in one form of the invention preferably from about 20 to about 24 carbon atoms. It is most preferred that the olefinic material be a mono-olefin. It is most preferred that the mono-olefin be an alpha-olefin, in which the double bond is located in a terminal ethylenic unit.

Commonly, such olefins would be available from a paraffinic media of the same carbon range. One route by which olefins in the 16 to 30 carbon number range are available is from dehydrogenating a mixture of paraffins in the same carbon number range, namely $C_{-16}$ to $C_{-30}$ paraffins. Such dehydrogenation may be carried out even if such a paraffin mixture has any appreciable olefin content, for example, an olefin content in the range of about 5 to 20%.

Process Conditions, Procedures, and Apparatus

The process of this invention can be carried out using the continuous reactive distillation column depicted in FIG. 1. In FIG. 1, a feed mixture of benzene and olefin, generally at a benzene-to-olefin molar ratio range of about 1:1 to 100:1 flows from feed pump 10 to feed inlet 14 via line 12. The feed mixture falls to packed mordenite catalyst bed 32 where alkylation in the presence of the fluorine-containing mordenite occurs. Alternatively, while not depicted in FIG. 1, the benzene and olefin can be introduced separately into the bed with mixing occurring in the bed, or the reactants can be mixed via an in-line mixer prior to introducing the reactants into the catalyst bed, or the reactants can be injected separately above the bed with mixing affected by use of standard packing above the bed, or the reactants can be sparged into the chamber above the bed. The catalyst bed 32 depicted in FIG. 1 for laboratory scale may be made of two lengths of 1.1 inch internal diameter tubing, the lengths being 9.5 inches and 22 inches. In the catalyst bed 32, the falling feed mixture also contacts rising vapors of unreacted benzene which has been heated to reflux in reboiler 42 by heater 40. Such rising vapors pass over thermocouple 38 which monitors temperature to provide feedback to heater 40. The rising vapors of benzene and/or olefin also pass through standard packing 36 (e.g., 7.5 inches of goodloe packing). The rising vapors heat thermocouple 30 which connects to bottoms temperature controller 28 which activates heater 40 when temperature drops below a set level.

Prior to startup, the system may be flushed with nitrogen which enters via line 54 and which flows through line 58. After startup, a nitrogen blanket is maintained over the system. Also prior to startup and during nitrogen flush, it may be desirable to heat catalyst bed 32 so as to drive off water from the fluorine-containing mordenite.

Residual water from the feed mixture or which otherwise enters the system is collected in water trap 24 upon being liquefied at condenser 21 (along with benzene vapor). If the feed is very dry (free of water) the water trap 24 may not be needed. Removing water leads to longer catalyst lifetime. Hence, the water trap 24 is optional. The same applies to FIG. 2. Condenser 21 is cooled via coolant such as water entering condenser 21 via port 22 and exiting via port 20. As needed, water in water trap 24 may be drained by opening drain valve 26.

As needed, when LAB content in reboiler 42 rises to a desired level, the bottoms LAB product may be removed from the system via line 47, using either gravity or bottoms pump 48 to withdraw the product. When product is so withdrawn, valve 44 is opened.

In FIG. 1, dip tube 46, which is optional, is employed to slightly increase the pressure in reboiler 42 to thereby raise the boiling point of benzene a degree or two. Likewise, a pressure generator 56 may be optionally employed to raise the pressure of the system. Other standard pressure increasing devices can be employed. Pressure can thus be increased in the system such that the boiling point of benzene increases up to about 200° C.

In FIG. 1, control mechanisms for heat shutoff 50 and pump shutoff 52 are depicted which serve to shut off heat and pump if the liquids level in the system rises to such levels. These control mechanisms are optional and may be included so that the catalyst bed does not come into contact with the bottoms of the reboiler.

Figure 2:
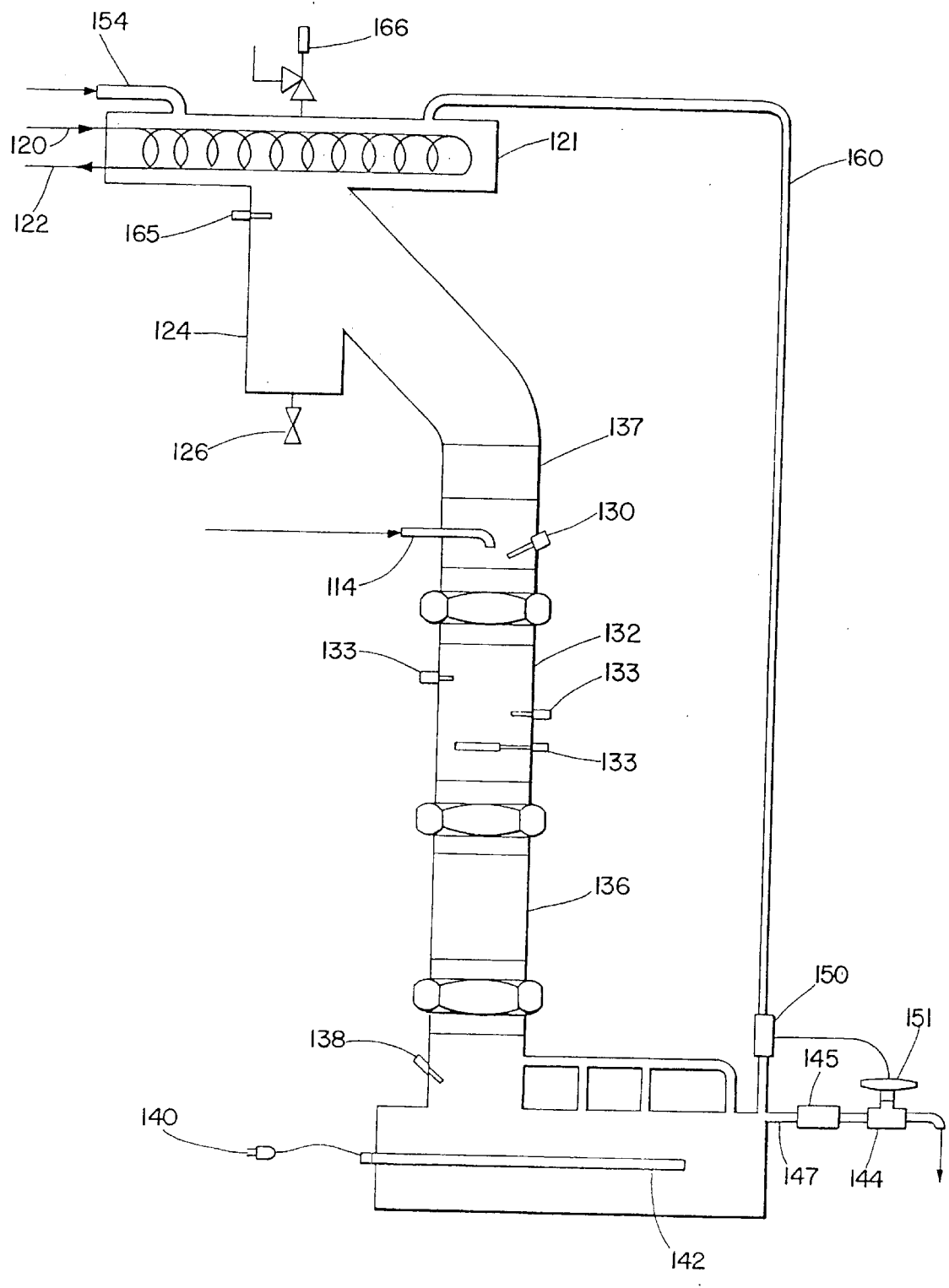
FIG. 2 shows a representation of a second continuous reactive distillation column employed in the practice of this invention.

In the practice of this invention in the alkylation of benzene, a wide variety of process conditions can be employed. In this regard, the temperature in the catalyst bed may vary depending on reactants, rate of introduction into the catalyst bed, size of the bed, and so forth. Generally, the bed is maintained at the reflux temperature of benzene depending on pressure. Typically, the temperature of the catalyst bed is above about 70° C., and most likely about 78° C. or more in order to have reasonable reaction rates, and about 200° C. or less to avoid degradation of reactants and products and to avoid deactivation of the catalyst by coke build-up. Preferably, the temperature is in the range from about 80° C to about 140° C. The process may be operated at a variety of pressures during the contacting step, with pressures of about atmospheric most typically being employed. When the process is operated using a system as depicted in FIGS. 1 and 2, the reboiler temperature is maintained such that benzene and olefin vaporize, the temperature varying depending on olefin, and generally being from about 80° C. to about 250° C. for olefins having 10 to 14 carbons. The composition of the reboiler will vary over time, but is generally set initially to have a benzene olefin ratio of about 10:1, with this ratio being maintained during the practice of this invention. The rate of introduction of feed into the catalyst bed may vary, and is generally at a liquid hourly space velocity ("LHSV") of about 0.05 $hr^{-1}$ to about 10 $hr^-$, more typically from about 0.05 $hr^{-1}$ to about 1 $hr^{-1}$. The mole ratio of benzene to olefin introduced into the catalyst bed is generally from about 1:1 to about 100:1. In commercial benzene alkylation operations, it is common to run at mole ratios of from about 2:1 to about 20:1, which can suitably be employed in the practice of this invention, and to charge said olefins as an olefin-paraffin mixture comprising 5% to 20% olefin content. Said olefin-paraffin mixtures are normally generated commercially through dehydrogenation of the corresponding paraffin starting material over a noble metal catalyst.

Another continuous reactive distillation apparatus is depicted in FIG. 2. In FIG. 2, the feed mixture enters the reactor via feed inlet 114. The feed mixture falls through the column into catalyst bed 132, wherein alkylation to form LAB occurs. A thermowell 133 monitors the temperature of said catalyst bed 132. The catalyst bed 132 may be optionally heated externally and is contained within 1-¼ inch stainless steel tubing. Goodloe packing is positioned at packing 136 and 137. LAB product, as well as unreacted benzene and olefin, fall through packing 136 into reboiler 142. In reboiler 142, electric heater 140 heats the contents of reboiler 142 such that heated vapors of benzene and olefin rise from the reboiler 142 to at least reach catalyst bed 132. As needed, the bottoms LAB product may be removed from reboiler 142 by opening bottoms valve 144 after passing through line 147 and filter 145. Residual water from the feed mixture, or which otherwise enters the system, may be condensed at condenser 121 which is cooled with coolant via inlet line 122 and exit line 120. The condensed water falls ; to water trap 124, which can be drained as needed by opening drain valve 126. Temperature in the system is monitored via thermocouples 138, 130, and 165. The system includes pressure release valve 166. A nitrogen blanket over the system is maintained by introduction of nitrogen gas via inlet line 154. Level control activator 150 activates bottoms level control valve 151 to open when the liquids level in the reboiler rises to the level control activator 150.

While the systems depicted in FIG. 1 and FIG. 2 show single catalyst bed systems, it must be appreciated that multi-catalyst bed reactors are within the scope of this invention, as well as multiple ports for inlet feeds, water traps, product removal lines, and so forth. Moreover, the process may be run in batch mode, or in other continuous processes using plugflow designs, trickle bed designs, and fluidized bed designs.

As average molecular weight of olefins increases, particularly when the average number of carbons is greater than about 15, the selectivity to the 2-isomer is less than for lower molecular weight olefins. It is thus preferred, although not absolutely necessary, that the product of the alkylation using HF-treated mordenite is sent to a second, finishing catalyst bed to improve yield. An example of such a second catalyst is HF-treated clay such as montmorillonite clay treated in accordance with the invention to have about 0.5% fluoride and calcined as stated earlier.

Variable 2-phenyl Isomer Content of Product Using the Mordenite of this Invention in Combination With a Second, Solid LAB Alkylation Catalyst The fluorine-containing mordenite of this invention generally produces LAB having high 2-phenyl isomer content, such as higher than about 70%. Conventional LAB alkylation technology does not, however, achieve these higher 2-phenyl isomer levels. The conventional LAB catalysts used most frequently are HF alkylation catalysts and aluminum chloride alkylation catalysts. Other alkylation catalysts in use today include, various zeolites, alumina-silica, various clays, as well as other catalysts. The use of hydrogen fluoride, for instance, produces about 16–18 percent of the 2-phenyl isomer in the product stream from the reactor. Using aluminum chloride as a catalyst produces LAB having between about 26–28 percent of the 2-phenyl isomer.

I have found that the mordenite of this invention can be used in combination with conventional solid LAB alkylation catalysts, such as silica-alumina (with or without fluorine treatment, such as disclosed in U.S. Pat. No. 5,196,574), clay and aluminum chloride. Since conventional LAB alkylation catalysts produce product having a 2-phenyl isomer content much less than that from the mordenite, combining the mordenite of this invention and a second solid alkylation catalyst may be used to achieve an LAB product having a higher 2-phenyl isomer content than which could be achieved by the conventional, solid LAB alkylation catalyst alone. In practice, the 2-phenyl isomer content of the final LAB product may be varied by adjusting the relative amounts of the two catalysts employed and/or the flow rate of reactants over each catalyst. For a given desired 2-phenyl isomer content of the product, the relative proportions of the two catalysts may vary depending on activity of each catalyst, the type and flow rates of the reactants, temperature, pressure, and other process variables.

Figure 3:
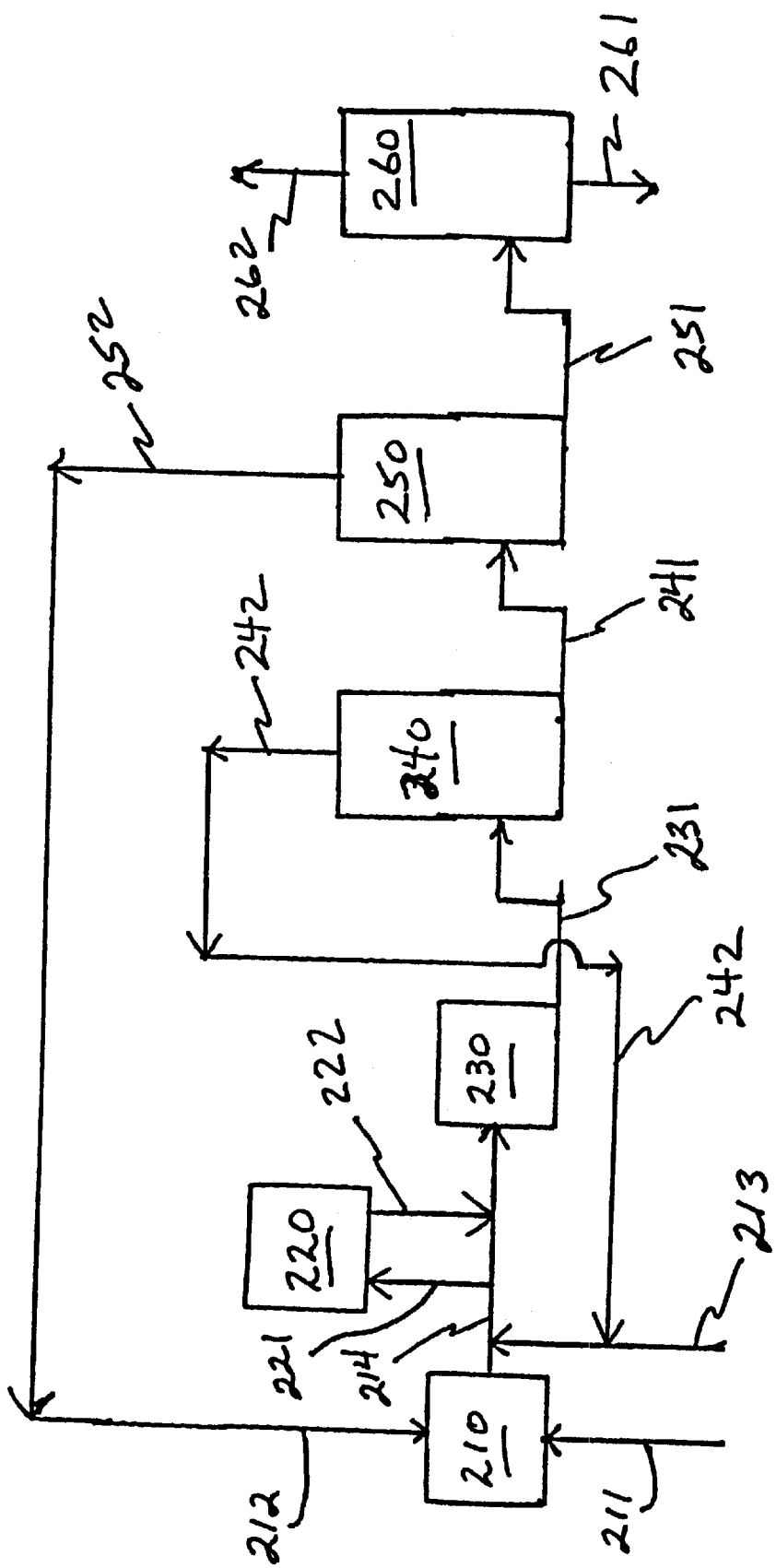
FIG. 3 shows a representative process scheme for one embodiment of this invention where a fluorine-containing mordenite is employed with a second, solid catalyst to achieve variable 2-phenyl isomer content depending on the relative proportions of the two catalysts.

FIG. 3 depicts a representative, non-limiting scheme for the practice of this invention. The catalysts (which may be used as a mixture or packed in series in the reactor 230, or loaded into two reactors aligned in series) are employed in amounts effective to achieve the desired level of 2-phenyl isomer content. If the catalysts are employed in series, whether in the same reactor or in multiple reactors, the amount of the first catalyst in the series is an amount relative to the amount and/or flow rate of the reactants that is insufficient to effect complete conversion of the reactants. The second catalyst may be used in any amount which will complete reaction of the reactants. The fluorine-containing mordenite may be either the first or second catalyst, preferably being in the first bed. Alternatively, either bed of catalyst in reactor 230 may be packed with a single catalyst, or a mixed bed of the two catalysts.

The scheme of FIG. 3 is shown in the context of LAB alkylation based on a feed from a paraffin dehydrogenation facility. Thus, in FIG. 3 fresh paraffin is fed to a conventional dehydrogenation apparatus 210 via line 211, with recycled paraffin being introduced from the paraffin column 250 via line 252. Dehydrogenated paraffin from the dehydrogenation apparatus 210 is then pumped into an alkylation reactor (or reactors) 230 that contains the fluorine-containing mordenite and a second, solid alkylation catalyst. The dehydrogenated paraffin feed may of course be supplied from any provider. The source of dehydrogenated paraffin (olefin) is not critical to the practice of this invention. LAB product from alkylation unit 230 may thereafter be purified by a series of distillation towers.

In this regard, alkylation effluent may be delivered to a benzene column 240 by way of line 231. It should be appreciated that the alkylation product may be sent offsite for purification. Further, the particular purification scheme used is not critical to the practice of this invention. The scheme depicted in FIG. 3 is instead representative of a typical commercial operation. In FIG. 3, unreacted benzene is distilled off from the crude LAB product. Benzene is then recycled to the alkylation reactor 230. The benzene-free LAB crude product from the benzene column 240 is pumped through line 241 to paraffin column 250 where any paraffin present is distilled off, with the distilled paraffin being recycled to paraffin dehydrogenation unit 210 via line 252. Paraffin-free crude LAB from the paraffin column 250 is transported to a refining column 260 where purified LAB is distilled and removed via line 262. Heavies (e.g., dialkylates and olefin derivatives) are withdrawn from refining column 260 via conduit 261.

It should be appreciated that columns 240, 250, and 260 may be maintained at conditions (e.g., pressure and temperature) well known to those of skill in the art and may be packed with conventional materials, if desired.

REPRESENTATIVE EXAMPLES

The following examples are illustrative of the present invention and are not intended to be construed as limiting the scope of the invention or the claims. In the examples, all reactants were commercial grades and used as received. The apparatus depicted in FIG. 1 was employed for examples 2–4. The apparatus depicted in FIG. 2 was used for example 5.

It is worthy of note that example 2 illustrates LAB production from paraffin dehydrogenate using the fluoride-treated mordenite catalyst of example B, where good catalyst life (250+hrs) is achieved without catalyst regeneration, while maintaining a 2-phenyl LAB selectivity of >70% and high LAB productivity without significant loss of fluoride. Comparative example 1, on the other hand, using untreated mordenite, with no fluoride added, shows a rapid decline in LAB production.

In addition, examples 3 and 4 illustrate LAB production using a 5:1 molar benzene/$C_{10}$–$C_{14}$ olefin feed mix and the fluoride-treated mordenite catalysts of Example B when operating at different LHSV's in the range of 0.2–0.4 $hr^{-1}$. Catalyst life may exceed 500 hours.

Example 5 illustrates LAB production with the fluoride-treated mordenite catalyst here the alkylation is conducted at higher temperatures and under pressure.

Examples 6–8 illustrate the performance of three HF-treated mordenite catalysts with different fluoride loading.

Example 9 shows how virtually no alkylation activity is observed with a highly-fluorinated mordenite.

Example A

Preparation of Fluoride-modified Mordenite

To 30 g of acidified mordenite (LZM-8, $SiO_2/Al_2O_3$ ratio 17; $Na_2O$ wt % 0.02, surface area 517 $m^2/g$, powder, from Union Carbide Corp.) was added 600 ml of 0.4% hydrofluoric acid solution, at room temperature. After 5 hours the solid zeolite was removed by filtration, washed with distilled water, dried at 120° C. overnight, and calcined at 538°C.

Example B

Preparation of a Hydrogen Fluoride-modified Mordenite

To 500 g of acidified, de-aluminized, mordenite (CBV-20A from PQ Corp.; $SiO_2/Al_2O_3$ molar ratio 20; $Na_2O$, 0.02 wt %; surface area 550 $m^2/g$, 1/16" diameter extrudates, that had been calcined at 538° C., overnight) was added a solution of 33 ml of 48% HF solution in 1633 ml of distilled water, the mix was cooled in ice, stirred on a rotary evaporator overnight, then filtered to recover the extruded solids. The extrudates were further washed with distilled water, dried in vacuo at 100° C., and then calcined at 538° C., overnight. Analyses of the treated mordenite showed a fluorine content of 1.2% and 0.49 meq/g of acidity.

Example 1

Preparation of Linear Alkylbenzenes Using a Hydrogen Fluoride-modified Mordenite Catalyst To a 500 ml flask, fitted with condenser and Dean Stark Trap was added 100 ml of benzene (reagent grade) plus 10 g of hydrogen fluoride-modified mordenite zeolite, prepared by the method of Example A. The mix was refluxed for 15–20 minutes to remove small amounts of moisture, then a combination of benzene (50 ml) plus 1-dodecene (10 g) was injected into the flask and the solution allowed to reflux for 3 hours.

Upon cooling, the modified mordenite catalyst was removed by filtration, the filtrate liquid flashed to remove unreacted benzene, and the bottoms liquid analyzed by gas chromatography. Analytical data for this catalyst are summarized in Table 1:

TABLE 1

| DODECENE CONV. (%) | LAB ISOMER DISTRIBUTION (%) | | | | | HEAVIES (%) | LINEAR LAB (LLAB) (%) |
|---|---|---|---|---|---|---|---|
| | 2-Ph | 3-Ph | 4-Ph | 5-Ph | 6-Ph | | |
| 99.7 | 79.9 | 16.6 | 0.8 | 1.3 | 1.3 | 0.2 | 95.9 |

Example 2

Preparation of Linear Alkylbenzenes From Paraffin Dehydrogenate Using a Hydrogen Fluoride-treated Mordenite Catalyst

In this example, benzene was alkylated with a sample of $C_{10}$–$C_{14}$ paraffin dehydrogenate containing about 8.5% $C_{10}$–$C_{14}$ olefins. Alkylation was conducted in a process unit as shown in FIG. 1.

Alkylation was conducted by first charging 500 ml of a benzene/paraffin dehydrogenate mix (10:1 molar ratio, benzene/$C_{10}$–$C_{14}$ olefin) to the reboiler and 250 cc of the HF-treated mordenite of example B to the 1.1" i.d. reaction zone. The mordenite was held in place using Goodloe packing. The reboiler liquid was then heated to reflux and a benzene plus $C_{10}$–$C_{14}$ paraffin dehydrogenate mix (10:1 molar ratio, benzene/$C_{10}$–$C_{14}$ olefin) continuously introduced into the unit above the catalyst column at the rate of 100 cc/hr. (LHSV=0.4 $hr^{-1}$).

Under steady state, reflux, conditions liquid product was continuously withdrawn water continuously taken off from the water trap. The crude liquid product was periodically analyzed by gas chromatography. The reboiler temperature was typically in the controlled range of 97–122° C. The column head temperature variability was 78–83° C. A summary of the analytical results may be found in Table 2.

After 253 hours of continuous operation, the recovered HF-treated mordenite catalyst contained 1.1% fluorine, an acidity of 0.29 meq/g and a water content of 0.3%.

TABLE 2

| Time on Stream (Hrs) | Sample | Alkylate Conc. (%) | 2-Phenyl Sel. (%) | $C_6H_6$ Conc. (%) |
|---|---|---|---|---|
| 0 | 0 | 1.4 | — | 32.3 |
| 2 | 1 | 3.4 | — | 19.7 |
| 4 | 2 | 5.8 | 74.9 | 16.6 |
| 6 | 3 | 6.6 | 75.8 | 25.2 |
| 32 | 4 | 7.9 | 80.7 | 27.0 |
| 56 | 5 | 7.8 | 82.7 | 27.0 |
| 69 | 6 | 7.3 | 81.4 | 27.4 |
| 94 | 7 | 6.5 | 82.0 | 27.8 |
| 118 | 8 | 6.0 | 78.4 | 27.7 |
| 142 | 9 | 5.9 | 81.3 | 26.9 |
| 166 | 10 | 5.4 | 81.5 | 27.3 |
| 207 | 11 | 5.3 | 81.3 | 26.1 |
| 229 | 12 | 5.1 | 81.1 | 27.4 |
| 253 | 13 | 4.9 | 81.4 | 28.1 |

Comparative Example 1

Preparation of Linear Alkylbenzenes From Paraffin Dehydrogenate Using an Untreated Mordenite Catalyst

Following the procedures of Example 9, the alkylation unit was charged with 250 cc of untreated, calcined, mordenite, (the starting mordenite of Example B), and the liquid feed comprised benzene plus $C_{10}$–$C_{14}$ paraffin dehydrogenate mix in a 10:1 molar ratio of benzene/$C_{10}$–$C_{14}$ recovered mordenite was analyzed to contain an acidity level of 0.29 meq/g and a water content of 2.1%. Performance results are summarized in Table 3.

TABLE 3

| Time on Stream (Hrs) | Sample | Alkylate Conc. (%) | 2-Phenyl Sel. (%) | $C_6H_6$ Conc. (%) |
|---|---|---|---|---|
| 0 | 0 | — | — | 11.2 |
| 2 | 1 | 6.50 | — | 9.9 |
| 4 | 2 | 7.16 | 73.2 | 17.1 |
| 6 | 3 | 7.09 | 73.1 | 26.4 |
| 22 | 4 | 8.61 | 73.9 | 26.6 |
| 31 | 5 | 10.49 | 67.4 | 15.8 |
| 46 | 6 | 7.39 | 75.0 | 27.7 |
| 70 | 7 | 6.39 | 75.1 | 28.5 |
| 93 | 8 | 6.08 | 73.6 | 23.0 |
| 144 | 9 | 5.21 | 73.6 | 15.8 |
| 157 | 10 | 4.40 | 73.9 | 26.2 |
| 180 | 11 | 3.06 | 69.6 | 27.1 |
| 204 | 12 | 1.32 | — | 19.5 |
| 228 | 13 | 1.32 | — | 33.3 |

Example 3

Preparation of Linear Alkylbenzenes From Paraffin Dehydrogenate Using a Hydrogen Fluoride-treated Mordenite Catalyst

Following the procedures of Example 2, the alkylation unit was charged with 250 cc of the HF-treated mordenite of Example B, and the liquid feed comprised a benzene plus $C_{10}$–$C_{14}$ paraffin dehydrogenate mix in a 5:1 molar ratio of benzene/$C_{10}$–$C_{14}$ olefin, the reboiler temperature was typically in the range of 122–188° C., the column head temperature 78–83° C. Performance results are summarized in Table 4.

After 503 hours of continuous operation, the recovered HF-treated mordenite catalyst showed a fluorine content of 1.0%. There were 0.35 meq/g of acidity, and the water content was 0.1%.

TABLE 4

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 0 | 0 | 1.0 | — | 8.9 | 1.1 |
| 2 | 1 | 3.5 | 61.8 | 0.3 | 3.5 |
| 4 | 2 | 7.1 | 72.1 | 0 | 7.1 |
| 6 | 3 | 6.8 | 76.7 | 7.2 | 7.3 |
| 34 | 4 | 8.4 | 79.7 | 14.3 | 9.8 |
| 71 | 5 | 7.2 | 81.8 | 14.6 | 8.5 |
| 96 | 6 | 6.5 | 80.8 | 15.5 | 7.7 |
| 119 | 7 | 6.3 | 80.6 | 15.1 | 7.4 |

TABLE 4-continued

| Time on Stream (Hrs) | Sample | Alkylate Conc. (%) | 2-Phenyl Sel. (%) | $C_6H_6$ Conc. (%) | Corrected[a] Alkylate Conc. (%) |
|---|---|---|---|---|---|
| 643 | 8 | 6.0 | 81.0 | 14.3 | 7.0 |
| 168 | 9 | 5.9 | 80.7 | 14.4 | 6.9 |
| 239 | 10 | 5.0 | 78.2 | 8.8 | 5.5 |
| 263 | 11 | 5.3 | 79.2 | 13.5 | 6.2 |
| 288 | 12 | 5.0 | 79.6 | 16.5 | 6.0 |
| 311 | 13 | 5.4 | 79.4 | 4.1 | 5.6 |
| 335 | 14 | 5.5 | 79.2 | 8.2 | 6.0 |
| 408 | 15 | 4.9 | 79.4 | 13.1 | 5.6 |
| 432 | 16 | 4.7 | 78.8 | 14.4 | 5.5 |
| 456 | 17 | 4.4 | 78.5 | 14.1 | 5.1 |
| 479 | 18[a] | 4.7 | 78.6 | 2.7[b] | 4.8 |
| 488 | 19[b] | 4.9 | 78.5 | 2.4[c] | 5.0 |
| 503 | 20[b] | 5.1 | 78.9 | 0.6[c] | 5.1 |

[a]Corrected for benzene in effluent sample.
[b]Applied pressure 8" $H_2O$
[c]Applied pressure 12" $H_2O$

Example 4

Preparation of Linear Alkylbenzenes From Paraffin Dehydrogenate Using a Hydrogen Fluoride-treated Mordenite Catalyst Following the procedures of Example 2, alkylation was conducted in the glassware unit of FIG. 1 complete with catalyst column, reboiler, condenser and controls. To the reaction zone was charged 500 cc of HF-treated mordenite of Example B. The liquid feed comprised a benzene plus $C_{10}$–$C_{14}$ paraffin dehydrogenate mix in a 5:1 molar ratio of benzene /$C_{10}$–$C_{14}$ olefin. The feed rate was 100 cc/hr (LHSV:0.2 $hr^{-1}$).

Under typical steady state, reflux, conditions, with a reboiler temperature range of 131–205° C. and a head temperature of 76–83° C. Performance results are summarized in Table 5.

TABLE 5

| Pressure (Inch $H_2O$) | Reboiler Temp./° C. | hours on stream | Sample | Alkylate Conc. (%) | 2-Phenyl Sel. | $C_6H_6$ Conc. (%) | Corrected[a] Alkylated Conc. (%) |
|---|---|---|---|---|---|---|---|
| 12 | 205 | 2 | 1 | 8.2 | 74.3 | 0.5 | 8.3 |
| 12 | 193 | 4 | 2 | 9.2 | 75.0 | 0.4 | 9.2 |
| 12 | 175 | 6 | 3 | 10.0 | 74.8 | 2.3 | 10.3 |
| 12 | 204 | 21 | 4 | 12.7 | 78.7 | 0.3 | 12.7 |
| 12 | 146 | 44 | 5 | 11.7 | 81.0 | 10.4 | 12.9 |
| 12 | 136 | 68 | 6 | 11.5 | 81.8 | 10.0 | 12.7 |
| 12 | — | 2–3 days | C[b] | 11.6 | 81.4 | 9.4 | 12.7 |
| 12 | 136 | 93 | 7 | 11.3 | 82.6 | 10.8 | 12.5 |
| 12 | — | 4–5 days | C-1[b] | 11.0 | 81.8 | 11.0 | 12.2 |
| 12 | 142 | 165 | 8 | 10.4 | 83.0 | 11.4 | 11.5 |
| 12 | 142 | 189 | 9 | 10.2 | 83.4 | 10.5 | 11.2 |
| 12 | 146 | 213 | 10 | 9.7 | 80.2 | 11.2 | 10.7 |
| 12 | 139 | 238 | 11 | 9.6 | 83.4 | 11.1 | 10.7 |
| 12 | 143 | 261 | 12 | 9.9 | 81.9 | 11.0 | 11.0 |
| 12 | 133 | 333 | 13 | 9.2 | 83.4 | 11.3 | 10.3 |
| 12 | 138 | 356 | 14 | 8.9 | 83.5 | 11.1 | 9.9 |
| 12 | 138 | 381 | 15 | 8.8 | 83.0 | 11.3 | 9.8 |
| 12 | 131 | 405 | 16 | 8.7 | 82.8 | 11.2 | 9.7 |

[a]Corrected for benzene in effluent sample
[b]Composite product

Example 5

Preparation of Linear Alkylbenzenes From Paraffin Dehydrogenate Using a Hydrogen Fluoride-treated Mordenite Catalyst Following the procedures of Example 2, alkylation of benzene with $C_{10}$–$C_{14}$ paraffin dehydrogenate was conducted using the stainless-steel unit of FIG. 2, complete with catalyst column, reboiler, condenser, and controls. About 250 cc or HF-treated mordenite of Example B was charged to the column. The liquid feed comprised benzene plus $C_{10}$–$C$_paraffin dehydrogenate mix in a 10:1 molar ratio of benzene/$C_{10}$–$C_{14}$ olefin. The LHSV varied from 0.2 to 0.4 $hr^{-1}$. Alkylation was conducted over a range of column and reboiler temperatures and a range of exit pressures. Performance results are summarized in Table 6.

TABLE 6

| Column Temp (° C.) | Pressure DIFF (psi) | Pressure EXIT (psi) | Pot Temp. (° C.) | Time (hr) | Sample (#) | Alkylate Conc. (%) | 2-Phenyl Sel. (%) | $C_6H_6$ Conc. (%) |
|---|---|---|---|---|---|---|---|---|
| 149–129 | 0.1 | 0 | 188 | 4 | 1 | 3.8 | — | 6.3 |
| 152–126 | 0 | 0 | 200 | 20 | 2 | 1.8 | — | 32.7 |
| 195–108 | 0 | 0 | 199 | 25 | 3 | 5.7 | — | 8.7 |
| 218–111 | 0 | 0 | 201 | 28 | 4 | 0.8 | — | 67.5 |
| 212–118 | 0 | 0 | 201 | 44 | 5 | 8.8 | 71.7 | 4.5 |
| 209–114 | 0.2 | 0 | 198 | 52 | 6 | 2.4 | — | 47.3 |
| 228–116 | 0 | 0 | 197 | 68 | 7 | 6.9 | 72.6 | 12.4 |
| 187–107 | 0.5 | 0 | 197 | 76 | 8 | 2.9 | 74.6 | 44.1 |
| — | — | — | — | 76 | 9[a] | 4.8 | 72.9 | 25.3 |
| — | — | — | — | — | 9C[b] | 6.8 | 72.2 | 1.0 |
| 174–107 | 0 | 0 | 178 | 6 | 10 | 4.1 | 79.2 | 54.9 |
| 170–106 | 0 | 0 | 172 | 22 | 11 | 2.0 | — | 59.8 |
| — | — | — | — | 28 | 12[a] | 6.6 | 76.8 | 26.8 |
| 142–107 | 0 | 0 | 136 | 31 | 13 | 4.8 | 67.9 | 18.9 |
| 141–110 | 0 | 0 | 138 | 47 | 14 | 4.4 | 65.9 | 16.9 |
| 142–110 | 0 | 0 | 136 | 55 | 15 | 5.0 | 63.9 | 16.6 |
| 168–111 | 0 | 0 | 131 | 71 | 16 | 4.1 | 64.8 | 16.7 |
| 170–108 | 0 | 0 | 150 | 79 | 17 | 5.0 | 72.0 | 8.8 |
| 175–113 | 0 | 0 | 143 | 95 | 18 | 5.9 | 68.1 | 15.2 |
| 145–106 | 0 | 5.2 | 188 | 14 | 19 | 3.2 | 60.2 | 9.0 |
| 149–108 | 0 | 4.2 | 186 | 20 | 20 | 4.8 | 66.3 | 12.0 |
| 160–118 | 0 | 11.7 | 213 | 29 | 21 | 4.2 | — | 6.7 |
| 160–119 | 0 | 9.3 | 210 | 44 | 22 | 5.2 | — | 6.6 |

[a]Composite product
[b]Stripped composite product

Examples 6, 7, 8

Preparation of Linear Alkylbenzenes Using Hydrogen Fluoride Modified Mordenite Catalysts With Different Fluoride Treatment Levels Following the procedures of Example 1, the alkylation unit was charged with benzene (100 ml), a 10 g sample of hydrogen fluoride-modified mordenite prepared by the procedure of Example B, plus a mix of benzene (50 ml) and 1-decene (10 g). Three HF-treated mordenites were tested, having the composition:

| Catalyst "C" | 0.25% HF on mordenite (CBV-20A) |
| Catalyst "D" | 0.50% HF on mordenite (CBV-20A) |
| Catalyst "E" | 1.0% HF on mordenite (CBV-20A) |

In each experiment samples of the bottoms liquid fraction were withdrawn at regular periods and subject to gas chromatography analyses. Performance results are summarized in Table 7.

TABLE 7

| CATALYST | TIME | % LLAB | % ISOS | % HVY | % 2Ph | % 3Ph | % 4Ph | % 5Ph | % 6 & 7Ph |
|---|---|---|---|---|---|---|---|---|---|
| D | 10 | 11.75 | 0.14 | 0 | 73.36 | 21.87 | 2.89 | 0.94 | 1.02 |
|   | 20 | 12.43 | 0.21 | 0 | 72.97 | 21.96 | 3.14 | 1.13 | 0.81 |
|   | 30 | 12.88 | 0.21 | 0 | 72.67 | 22.13 | 3.03 | 1.16 | 1.01 |
|   | 40 | 12.27 | 0.22 | 0 | 73.02 | 21.92 | 2.85 | 1.06 | 1.14 |
|   | 50 | 12.15 | 0.98 | 0 | 72.46 | 21.67 | 3.21 | 1.17 | 1.49 |
|   | 50 | 12.24 | 1.01 | 0 | 72.53 | 21.63 | 3.23 | 1.12 | 1.44 |
|   | 60 | 12.28 | 0.21 | 0 | 72.96 | 22.07 | 2.93 | 1.14 | 0.91 |
|   | 60 | 11.98 | 0.21 | 0 | 72.97 | 22.21 | 2.93 | 1.17 | 0.83 |
| C | 10 | 12.2  | 0.18 | 0 | 72.54 | 22.46 | 3.21 | 0.98 | 0.82 |
|   | 20 | 12.7  | 0.39 | 0 | 71.51 | 22.61 | 2.91 | 1.02 | 2.13 |
|   | 30 | 12.52 | 0.21 | 0 | 71.96 | 22.68 | 2.96 | 1.04 | 1.36 |
|   | 40 | 12.75 | 0.21 | 0 | 71.84 | 22.67 | 3.22 | 1.02 | 1.25 |
|   | 50 | 12.98 | 0.21 | 0 | 71.57 | 22.81 | 3.16 | 1.08 | 1.39 |
|   | 60 | 12.54 | 0.21 | 0 | 71.45 | 22.81 | 3.19 | 1.12 | 1.44 |
|   | 60 | 12.33 | 0.21 | 0 | 71.61 | 22.87 | 2.92 | 1.05 | 1.31 |
| E | 10 | 10.56 | 0.05 | 0 | 75.19 | 19.41 | 2.18 | 3.22 |  |
|   | 20 | 12.95 | 0.15 | 0 | 74.36 | 19.23 | 3.01 | 3.4  |  |
|   | 30 | 13.44 | 0.18 | 0 | 74.11 | 19.42 | 3.2  | 3.27 |  |
|   | 40 | 13.16 | 0.15 | 0 | 074.16| 19.38 | 3.12 | 3.34 |  |
|   | 50 | 13.1  | 0.15 | 0 | 74.43 | 19.16 | 3.21 | 3.28 |  |
|   | 60 | 12.83 | 0.15 | 0 | 74.28 | 19.49 | 2.88 | 3.35 |  |
|   | 60 | 12.87 | 0.16 | 0 | 73.82 | 19.97 | 2.8  | 3.2  |  |

Example 9

Illustrating the Inactivity of a Heavily Loaded Hydrogen-fluoride Modified Mordenite Catalyst Following the procedures of Example 2, the alkylation unit was 100 cc of a hydrogen floride-treated mordenite (CBV-20A) prepared by the method of Example B but having a much higher loading of HF (fluoride content 4.8%). The acidity of said HF-treated mordenite was 0.15 meq/g. No significant amount of alkylated product was detected in the reactor effluent by gas chromatography.

Thus, the foregoing examples are illustrative of the preparation of catalysts and alkylbenzenes according to the invention. In cases where it is desired to append olefins having carbon numbers in the range of 18 to 30, the catalysts and reaction conditions and process procedures are identical to those provided above, with such well known variables as distillation temperatures being readily adjusted accordingly to the desires of the operator of ordinary skill in this art.

Example 10

Preparation of High Molecular Weight Alkylbenzenes Using Fluoridated Clay

This example illustrates the preparation of high molecular weight alkylbenzenes in the $C_{18}$ to $C_{24}$ range using 16×30 mesh fluoridated clay catalyst. For this example, the catalyst is first desired under 30-mmHg vacuum at 120–130° C. for 4 hours prior to use. To a 500 ml round bottom flask fitted with a condenser, Dean Stark trap, and a thermometer, was added 10 grams of catalyst and 80 ml of reagent benzene. The contents were magnetically stirred and heated to benzene reflux. About 25 ml of azeotrope was removed and 10 grams of $C_{18}$ to $C_{24}$ olefin was added while being stirred. The reaction is monitored by GC or bromine number. The reaction was monitored by taking samples every one hour and was stopped after three hours. The cooled reaction mixture was filtered to remove catalyst and benzene was removed by distillation. The bormine number of colorless alkylate product was determined to asses the olefin conversion and the product was also analyzed using gas chromatography. An olefin conversion of 78% was achieved.

Example 11

Preparation of High Molecular Weight Alkylbenzenes Using Fluoridated Clay

Another run was carried out in accordance with the procedures outlined for Example 10 using a feedstock of $C_{20}$–$C_{24}$ olefin and fluoridated clay as catalyst. An olefin conversion of 99% was obtained.

Example 12

Preparation of High Molecular Weight Alkylbenzenes Using Fluoridated Clay

Another run was carried out in accordance with the procedures outlined for Example 10 using a feedstock of $C_{24}$–$C_{28}$ olefin using fluoridated clay as catalyst. An olefin conversion of 82% was achieved with a 2-phenyl isomer content of 30%.

Example 13

Preparation of High Molecular Weight Alkylbenzene

This example illustrates the preparation of high molecular weight alkylbenzene from a feedstock comprising $C_{20}$–$C_{24}$, using a mordenite catalyst produced in accordance with the invention. The acidic form of the catalyst from example 4 above was dried and calcined, and was re-dried as in example 1 prior to using conditions as in example 12 above. An olefin conversion of 98% was achieved, with a 74% 2-phenyl isomer content.

Example 14

Preparation of High Molecular Weight Alkylbenzene

One more run was carried out using fluoridated mordenite catalyst according to example 4 and $C_{24}$–$C_{28}$ olefin under conditions employed in example 12. An olefin conversion of 68% was achieved, having a 70% 2-phenyl isomer content.

Example 15

Preparation of High Molecular Weight Alkylbenzene

This example illustrates the preparation of $C_{20}$–$C_{24}$ alkylate from $C_{20}$–$C_{24}$ olefins using hydrogen fluoride treated mordenite catalyst. In this example, benzene was alkylated with $C_{20}$–$C_{24}$ olefins and the alkylation was conducted in a process unit as shown in FIG. 1. The reactor was filled with 300 ml of 0.1%-fluoridated mordenite. The catalyst was held in position by Goodloe packing, and the alkylation was conducted by first charging 500-ml benzene/paraffin mixture in a 3:1 ratio to the reboiler. The reboiler charge was heated to reflux, and about 15 ml of benzene azeotrope was drained from the overhead trap to ensure anhydrous conditions in the reactor. Overhead Dean-Stark trap draining was done for every 24 hours. The feed mixture containing benzene and $C_{20}$–$C_{24}$ olefin in 10:1 mole ratio was introduced continuously above the catalyst bed where feed comes in contact with refluxing benzene vapors. Benzene azeotrope is collected into the overhead trap and dry reactants enter into the catalyst bed to form the alkylate. At steady state a sample is withdrawn from the reboiler, benzene was removed and analyzed for olefin conversion by bromine number method and 2-phenyl isomer content by gas chromatography.

| Bromine Number | Time, Hrs | % Olefin Conversion | Comments |
| --- | --- | --- | --- |
| 23.1 | 0 | 0 | starting olefin |
| 0.36 | 68 | 98.44 | Benzene/Olefin ratio of 10 |
| 0.31 | 136 | 98.67 | Overhead drained every 24 hrs. |
| 0.22 | 304 | 99.06 | |
| 0.12 | 472 | 99.48 | |
| 0.18 | 544 | 99.2 | |
| 0.14 | 592 | 99.4 | |

Example 16

Preparation of High Molecular Weight Alkylbenzene

In this example, to improve the performance of the reactor and to prolong the life of the catalyst, draining frequency of the overhead trap was increased from once every 24 hours to once in every 8 hours.

| Bromine Number | Time, Hrs | % Olefin Conversion | Comments |
|---|---|---|---|
| 0.08 | 736 | 99.65 | Overhead drained every 8 hrs. |
| 0.02 | 808 | 99.9 | |
| 0.26 | 976 | 98.9 | No overhead drained during weekend |
| 0.08 | 1120 | 99.65 | |
| 0.19 | 1192 | 99.18 | Overhead drained once a day |

Example 17

Preparation of High Molecular Weight Alkylbenzene

In this example, the benzene olefin ratio of 10 was lowered to 5 to improve the efficiency of the operation. The draining of overhead trap was done once in every 8 hours.

| Bromine Number | Time, Hrs | % Olefin Conversion | Comments |
|---|---|---|---|
| 0.13 | 1360 | 99.44 | Benzene/Olefin ratio of 5 |
| 0.1 | 1432 | 99.6 | |
| 0.21 | 1504 | 99.1 | |
| 0.05 | 1592 | 99.78 | |

Hydrocarbon and other base oils such as the vegetable oils are known to be rarely used in their pure forms in any application, but rather contain various chemical additives designed to increase the performance of such oils, or to extend the useful lives of either the oils themselves or the equipment in which they are designed to function. In this regard, the prior art teaches the use of various oil additives which include without limitation:detergents, dispersants, anti-wear agents, extreme pressure additives, antioxidants, corrosion inhibitors, viscosity modifiers, pour point depressants, antifoam agents, friction modifiers, metal deactivators, water scavengers, free radical scavengers, and compatibilizers.

Although the present invention has been described largely in reference to the alkylation of benzene using olefins as an alkylating agent, it should be appreciated that substituted benzenes are also useful as starting materials within the context of the present invention, provided that the chemical groups appended to the benzene ring are not prohibitively de-activating of the benzene ring structure. In this regard, toluene is a functionally equivalent starting material which may be used in place of all or part of the benzene employed. Other substituted benzenes such as xylenes are also useful in this regard, as well as ethylbenzene, propylbenzene, and butylbenzene.

In cases where a substituted benzene is alkylated in accordance with the principles of this invention, the reaction product consists predominantly of para-substituted reaction products, with some ortho substitution. Subsequent sulfonation of such a mixture to provide sulfonate derivatives results in a mixture of sulfonates or their salts or esters as well. These materials may be conveniently described by the formula:

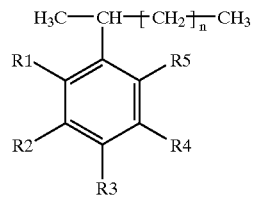

in which n may be any integer between 13 and 27, and in which $R_1$, $R_2$, $R_3$, R4, and $R_5$ are each independently selected from the group consisting of: hydrogen, methyl, ethyl, propyl, butyl, sulfonic acid, sulfonate, and salts and esters thereof.

Detergents Useful in Hydrocarbon Oils

One popular class of detergents used in lubricating oils, cutting fluids, and the like are the oil soluble sulfonates. Within this broad class are the aromatic sulfonates of the type described in this specification, particularly the LAB sulfonates. These materials are preferred because of their effectiveness and compatibility with other components found in finished oil products, their widespread availability, and relatively low cost. Additionally, many of these detergent materials are anionic in nature, which means that any one of a wide range of selected cationic species may accompany the anionic detergent, which is of particular benefit when it is desired to incorporate other metals into the composition. The most commonly used salts of these acids in hydrocarbon oils are the sodium, potassium, lithium, calcium, magnesium, strontium and barium salts. The "basic salts" are those metal salts known to the art wherein the metal is present in a stoichiometrically larger amount than that necessary to neutralize the acid. The calcium- and barium-overbased petrosulfonic acids are typical examples of such basic salts.

The terms "overbased," "superbased," and "hyperbased," are terms of art which are generic to well known classes of the metallic sulfonates and other materials. These overbased materials have also been referred to as "complexes," "metal complexes," "high-metal containing salts," and the like. Overbased materials are characterized by a metal content in excess of that which would be present according to the stoichiometry of the metal and the particular organic compound reacted with the metal, e.g., a sulfonic acid. Thus, if a monosulfonic acid such as an LAB sulfonate is neutralized with a basic metal compound, e.g., calcium hydroxide, the "normal" metal salt produced will contain one equivalent of calcium for each equivalent of acid. However, as is well known in the art, various processes are available which result in an inert organic liquid solution of a product containing more than the stoichiometric amount of metal. The solutions of these products are referred to herein as overbased materials. Following these procedures, the sulfonic acid or an alkali or alkaline earth metal salt thereof can be reacted with a metal base and the product will contain an amount of metal in excess of that necessary to neutralize the acid, for example, 4.5 times as much metal as present in the normal salt or a metal excess of 3.5 equivalents. The actual stoichiometric excess of metal can vary considerably, for example, from about 0.1 equivalent to about 30 or more equivalents depending on the reactions, the process conditions, and the like. These overbased materials useful in preparing the disperse systems will contain from about 3.5 to about 30 or more equivalents of metal for each equivalent of material which is overbased. In the present specification and claims the term "overbased" is used to designate materials containing a stoichiometric excess of metal and is, therefore, inclusive of those materials which have been referred to in the art as overbased, superbased, hyperbased, etc., as discussed supra.

The overbased materials are prepared by treating a reaction mixture comprising the organic material to be overbased, a reaction medium consisting essentially of at least one inert, organic solvent for said organic material, a stoichiometric excess of a metal base, and a promoter with an acidic material. The methods for preparing the overbased materials as well as an extremely diverse group of overbased materials are well known in the prior art and are disclosed for example in the following U.S. Pat. Nos.: 2,616,904; 2,616,905; 2,616,906; 2,616,911; 2,616,924; 2,616,925; 2,617,049; 2,695,910; 2,723,234; 2,723,235; 2,723,236; 2,760,970; 2,767,164; 2,767,209; 2,777,874; 2,798,852; 2,839,470; 2,856,359; 2,859,360; 2,856,361; 2,861,951; 2,883,340; 2,915,517; 2,959,551; 2,968,642; 2,971,014; 2,989,463; 3,001,981; 3,027,325; 3,070,581; 3,108,960; 3,147,232; 3,133,019; 3,146,201; 3,152,991; 3,155,616; 3,170,880; 3,170,881; 3,172,855; 3,194,823; 3,223,630; 3,232,883; 3,242,079; 3,242,080; 3,250,710; 3,256,186; 3,274,135; 3,492,231; and 4,230,586. These patents disclose processes, materials which can be overbased, suitable metal bases, promoters, and acidic materials, as well as a variety of specific overbased products useful in producing the disperse systems of this invention and are, accordingly, incorporated herein by reference. Other detergents known to those skilled in the art are useful as a component of a composition according to the invention in addition to the LAB based detergents described herein.

Dispersants Useful in Hydrocarbon Oils

Although a dispersant used in a hydrocarbon oil may be a multifunctional material that can confer other beneficial properties to a base oil, dispersants are primarily used in hydrocarbon oils for their ability to maintain small particles of dirt, combustion products, metal fines, etc. in the liquid phase, to prevent deposition and accumulation of sludges in places where eddy currents exist in various equipment and wares.

The use of acylated nitrogen compounds as dispersants in lubricants is disclosed in numerous patents, including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; 3,804,763; and 4,234,435.

The book "Lubricant Additives" by M. W. Ranney, published by Noyes Data Corporation of Parkridge, N.J. (1973), discloses a number of overbased metal salts of various sulfonic acids which are useful as detergent/dispersant in lubricants. The book also entitled "lubricant Additives" by C. V. Smallheer and R. K. Smith, published by the Lezius-Hiles Co. of Cleveland, Ohio (1967), similarly discloses a number of overbased sulfonates which are useful as dispersants. U.S. Pat. No. 4,100,082 discloses the use of neutral or overbased metal salts of organic sulfur acids as detergent/dispersants for use in fuels and lubricants.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions and functional fluids of this invention. The following are illustrative of dispersants, not delimitive of the term, and are incorporated by reference herein:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in many U.S. Pat. Nos., including 3,219,666; 4,234,435; and 4,938,881. These include the products formed by the reaction of a polyisobutenyl succinic anhydride with an amine such as a polyethylene amine.

(2) Reaction products of relatively high molecular weight aliphatic or alicyclic halides with amines, preferably oxyalkylene polyamines. These may be characterized as "amine dispersants" and examples thereof are described for example, in the following U.S. Pat. Nos.:3,275,554; 3,438,757; 3,454,555; and 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants." The materials described in the following U.S. Pat. Nos. are illustrative: 3,649,229; 3,697,574; 3,725,277; 3,725,480; 3,726,882; and 3,980,569.

(4) Products obtained by post-treating the amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos. 3,639,242; 3,649,229; 3,649,659; 3,658,836; 3,697,574; 3,702, 757; 3,703,536; 3,704,308; and 3,708,422.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos. 3,329,658; 3,449,250; 3,519,565; 3,666,730; 3,687,849; and 3,702,300.

Antiwear Agents

A composition according to this invention may also include a sulfur-, phosphorus-, or sulfur- and phosphorus-containing antiwear agent. The term antiwear agent is used to refer to compounds which provide wear protection properties to lubricating compositions and functional fluids. Antiwear agents are useful in controlling wear and may sometimes also act as extreme pressure agents and as antioxidants. These antiwear agents include sulfurized organic compounds, hydrocarbyl phosphates, phosphorus-containing amides, phosphorus-containing carboxylic esters, phosphorus-containing ethers, and dithiocarbamate-containing compounds. Examples of hydrocarbyl phosphates include hydrocarbyl thiophosphates. Thiophosphates may contain from one to about three sulfur atoms, preferably one or two sulfur atoms. Thiophosphates are prepared by reacting one or more phosphites with a sulfurizing agent including sulfur, sulfur halides, and sulfur containing compounds. Salts of thiophosphates include zinc dithiophosphates. Other antiwear agents known to those skilled in the art are useful as a component of a composition according to the invention. Other dispersants known to those skilled in the art are useful as a component of a composition according to the invention.

Anti-oxidants

A particularly valuable class of additives known as anti-oxidants are widely used in lubricating oil formulations, cutting oils, and functional fluids. Antioxidants are materials which inhibit oxidative decomposition of the oil under consideration. Although several examples are given below, these examples should be considered exemplary only of the wide variety of antioxidants which may be usefully combined with the detergent components of this invention.

In U.S. Pat. No. 2,282,710 to Dietrich issued May 12, 1942 it is known that stabilization of petroleum hydrocarbons against the deleterious catalytic action of metals may be obtained by compositions containing both a nitrogen and a sulfur functional group. Various cyclic, aromatic and linear carbon configurations are shown in the sulfur and nitrogen containing molecules of Dietrich. Dietrich discloses preparing his compositions by the use of ethyleneimine. Dietrich further states that his compounds are particularly effective in retarding the formation of products corrosive to metals, and particularly cadmium, silver, copper, lead and like bearing alloys under normal service conditions.

German OLS 1,066,019 published Sep. 24, 1959 by Holtschmitt et al describes various condensation products of thioglycol and nitrogen containing materials. Holtschmitt shows his compounds as containing free hydroxyl groups. Holtschmitt further discloses the use of aromatic amines containing a short aliphatic group on the aromatic ring, e.g. toluidine.

It is known from an article entitled Thioglycol Polymers 1 Hydrochloric Acid-Catalysed Auto Condensation of Thiodiglycol by Woodward, Journal of Polymer Science the OL XLI, Pages 219–223 (1959), that the properties of a sulfur and oxygen containing compound allow end-to-end condensation. It is further known from the Woodward article that multiple sulfur linkages within the molecule, e.g. disulfides, trisulfides, and the like may be obtained.

It is further known that various amines may be utilized in antioxidant compositions. Phenothiazine compounds are known in lubricant products from U.S. Pat. No. 2,781,318 issued Feb. 12, 1957 to Cyphers. The alkyl phenothiazines of Cyphers are alkylated on the phenylene rings of the phenothiazine structure. Cyphers does not show or suggest the alkylation of the amine nitrogen in phenothiazine. The Cyphers patent is directed to the utility of phenothiazine as an antioxidant and corrosion inhibiting additive for ester, polyester, polyether and other synthetic lubricants.

U.S. Pat. No. 3,536,706 issued Oct. 27, 1970 to Randell suggests that phenothiazines may be used as additives for synthetic lubricants. The phenothiazines particularly described by Randell are those containing tertiary alkyl substituents having from 4 to 12 carbon atoms on the aryl groups which make up the phenothiazine structure. Randell also discloses fused rings on the two phenylene groups which make up the phenothiazine structure. Stated otherwise, Randell allows the utilization of naphthalene for at least one of the two aryl groups in the phenothiazine structure. U.S. Pat. No. 3,803,140 issued to Cook et al on Apr. 9, 1974 describes various tertiary alkyl derivatives of phenothiazine. N-alkyl substitution or N-alkenyl substitution is described on the phenothiazine structure. Ring alkylation when the phenothiazine is in the free nitrogen form is also shown. Cook et al express a preference for non-N substituted phenothiazine derivatives.

Cook et al also suggest that organic materials which are susceptible to oxidative degradation may benefit through the use of the compounds of their invention. Such uses include antioxidants for aliphatic hydrocarbons such as gasoline, lubricating oils, lubricating greases, mineral oils, waxes, natural and synthetic polymers such as rubber, vinyl, vinylidene, ethers, esters, amides and urethanes. The compounds of Cook et al are also suggested for stabilizing aldehydes and unsaturated fatty acids or esters thereof. Still further utilities suggested by Cook et al include the stabilization of organo-metalloid substances such as silicone polymers. Another class of uses of the compounds of Cook et al include the stabilization of vitamins, essential oils, ketones and ethers.

Normant in U.S. Pat. No. 3,560,531 issued Feb. 2, 1971, describes metallation of materials having active hydrogens including phenothiazine. U.S. Pat. No. 3,344,068 issued Sep. 26, 1967, to Waight et al describes antioxidants for ester-based lubricants. Waight et al's compounds have an N-hydrocarbyl substituted phenothiazine structure. The N-substituted phenothiazine compounds of Waight et al are also substituted in at least one position on the fused aromatic nuclei. A second required component in the compositions of Waight et al is a secondary aromatic amine having two aromatic groups attached to the nitrogen atom.

The preparation of alkylthioalkanols which are useful as intermediates for preparing the compounds of the present invention are described in U.S. Pat. No. 4,031,023 to Musser et al. The Musser et al patent was issued Jun. 21, 1977 and is assigned to The Lubrizol Corporation.

U.S. Pat. No. 2,194,527 to Winthrop et al which issued Nov. 24, 1959, describes pharmaceutical compounds such as omega-(10-phenothiazinyl)alkyl di-alkyl sulfonium salts which are useful as spasmolytics and in particular antihistaminics. U.S. Pat. No. 3,376,224 issued Apr. 2, 1968 to Elliott et al describes phenothiazine derivatives which are stated to be N-substituted methylene compounds which contain an ether linkage between the methylene group and an alkyl or cycloalkyl radical. According to Elliott et al, the alkyl or cycloalkyl radical may carry an alkoxy or other non-reactive substituent.

U.S. Pat. No. 4,915,858 describes a composition of matter which is the amine terminated reaction product obtained from two equivalents of a secondary aromatic monoamine with at least two equivalents of a betathiodialkanol. Other antioxidants known to those skilled in the art are useful as a component of a composition according to the invention.

Corrosion Inhibitors

Corrosion-inhibiting agents are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dioctylphosphorodithioate, zinc dicyclohexylphosphorodithioate, barium di(heptylphenyl) phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol. Other corrosion inhibitors known to those skilled in the art are useful as a component of a composition according to the invention.

Viscosity Modifiers

Viscosity modifiers generally are polymeric materials characterized as being hydrocarbon-based polymers generally having number average molecular weights between about 25,000 and 500,000 more often between about 50,000 and 200,000. Such materials are typically added to a hydrocarbon based oil and the oil is heated, with agitation, until the polymeric material is dissolved.

Polyisobutylene has been used as a viscosity modifier in lubricating oils. Polymethacrylates (PMA) are prepared from mixtures of methacrylate monomers having different alkyl groups. Most PMA's are viscosity-modifiers as well as pour point depressants. The alkyl groups may be either straight chain or branched chain groups containing from 1 to about 18 carbon atoms.

Ethylene-propylene copolymers, generally referred to as OCP can be prepared by copolymerizing ethylene and propylene, generally in a solvent, using known catalysts such as a Ziegler-Natta initiator. The ratio of ethylene to propylene in the polymer influences the oil-solubility, oil-thickening ability, low temperature viscosity, pour point depressant capability and engine performance of the product. The common range of ethylene content is 45–60% by weight and typically is from 50% to about 55% by weight. Some commercial OCP's are terpolymers of ethylene, propylene and a small amount of nonconjugated diene such as 1,4-hexadiene. In the rubber industry, such terpolymers are referred to as EPDM (ethylene propylene diene monomer). The use of OCP's as viscosity modifiers in lubricating oils has increased rapidly since about 1970, and the OCP's are currently one of the most widely used viscosity modifiers for motor oils.

Esters obtained by copolymerizing styrene and maleic anhydride in the presence of a free radical initiator and thereafter esterifying the copolymer with a mixture of $C_{4-18}$ alcohols also are useful as viscosity modifying additives in motor oils. The styrene esters generally are considered to be multifunctional premium viscosity modifiers. The styrene esters in addition to their viscosity modifying properties also are pour point depressants and exhibit dispersancy properties when the esterification is terminated before its completion leaving some unreacted anhydride or carboxylic acid groups. These acid groups can then be converted to imides by reaction with a primary amine.

Hydrogenated styrene-conjugated diene copolymers are another class of commercially available viscosity modifiers for motor oils. Examples of styrenes include styrene, alpha-methyl styrene, ortho-methyl styrene, meta-methyl styrene, para-methyl styrene, para-tertiary butyl styrene, etc. Preferably the conjugated diene contains from four to six carbon atoms. Examples of conjugated dienes include piperylene, 2,3-dimethyl-1,3-butadiene, chloroprene, isoprene and 1,3-butadiene, with isoprene and butadiene being particularly preferred. Mixtures of such conjugated dienes are useful.

The styrene content of these copolymers is in the range of about 20% to about 70% by weight, preferably about 40% to about 60% by weight. The aliphatic conjugated diene content of these copolymers is in the range of about 30% to about 80% by weight, preferably about 40% to about 60% by weight.

These copolymers typically have number average molecular weights in the range of about 30,000 to about 500,000, preferably about 50,000 to about 200,000. The weight average molecular weight for these copolymers is generally in the range of about 50,000 to about 500,000, preferably about 50,000 to about 300,000.

The above described hydrogenated copolymers have been described in the prior art such as in U.S. Pat. Nos. 3,551,336; 3,598,738; 3,554,911; 3,607,749; 3,687,849; and 4,181,618 which are hereby incorporated by reference for their disclosures of polymers and copolymers useful as viscosity modifiers in oil compositions according to this invention. For example, U.S. Pat. No. 3,554,911 describes a hydrogenated random butadiene-styrene copolymer, its preparation and hydrogenation. The disclosure of this patent is incorporated herein by reference. Hydrogenated styrene-butadiene copolymers useful as viscosity modifiers in the lubricating oil compositions of the present invention are available commercially from, for example, BASF under the general trade designation "Glissoviscal". A particular example is a hydrogenated styrene-butadiene copolymer available under the designation Glissoviscal 5260 which has a molecular weight, determined by gel permeation chromatography, of about 120,000. Hydrogenated styrene-isoprene copolymers useful as viscosity modifiers are available from, for example, The Shell Chemical Company under the general trade designation "Shellvis". Shellvis 40 from Shell Chemical Company is identified as a diblock copolymer of styrene and isoprene having a number average molecular weight of about 155,000, a styrene content of about 19 mole percent and an isoprene content of about 81 mole percent. Shellvis 50 is available from Shell Chemical Company and is identified as a diblock copolymer of styrene and isoprene having a number average molecular weight of about 100,000, a styrene content of about 28 mole percent and an isoprene content of about 72 mole percent. Other viscosity modifiers known to those skilled in the art are useful as a component of a composition according to the invention.

Pour Point Depressants

Pour point depressants may also be included in a formulation according to the invention. They are a particularly useful type of additive often included in the lubricating oils and functional fluids such as cutting oils or other lubricants, and often comprise oil-soluble polymers. Examples of pour point depressants include those on page 8 of "Lubricant Additives" by C. V. Smalheer and R. Kennedy Smith (Lesius-Hiles Company Publishers, Cleveland, Ohio, 1967, which book is incorporated in its entirety herein by reference thereto). Other pour point depressants known to those skilled in the art are useful as a component of a composition according to the invention.

Antifoam Agents

Anti-foam agents may be used to reduce or prevent the formation of stable foam and include silicones or organic polymers. Examples of these and additional anti-foam compositions are described in "Foam Control Agents", by Henry T. Kerner (Noyes Data Corporation, 1976), pages 125–162, which book is incorporated in its entirety herein by reference thereto. Other antifoam agents known to those skilled in the art are useful as a component of a composition according to the invention.

Friction Modifiers

The oil compositions of the present invention also may contain at least one friction modifier to provide the lubricating oil with the proper frictional characteristics for a given application. Various amines, particularly tertiary amines are effective friction modifiers. Examples of tertiary amine friction modifiers include N-fatty alkyl-N,N-diethanol amines, N-fatty alkyl-N,N-diethoxy ethanol amines, etc. Such tertiary amines can be prepared by reacting a fatty alkyl amine with an appropriate number of moles of ethylene oxide. Tertiary amines derived from naturally occurring substances such as coconut oil and oleoamine are available from Armour Chemical Company under the trade designation "Ethomeen". Particular examples are the Ethomeen-C and the Ethomeen-O series. Sulfur-containing compounds such as sulfurized $C_{12-24}$ fats, alkyl sulfides and polysulfides wherein the alkyl groups contain from 1 to 8 carbon atoms, and sulfurized polyolefins also may function as friction modifiers in the lubricating oil compositions of the invention. Other friction modifiers known to those skilled in the art are useful as a component of a composition according to the invention.

Base Oils

The present invention is broad with respect to the selection of base oil component used in its blending. Typically, compositions according to the invention comprise a base oil as a major component of the composition. For purposes of this specification and the appended claims the term "base oil" as used herein is intended to include those materials which are recognized as possessing lubricity characteristics by those of ordinary skill in the art. Such materials include, without limitation, materials falling within the following classes: 1) lubricity agents such as synthetic polymers (e.g., polyisobutene having a number average molecular weight in the range of about 750 to about 15,000, as measured by vapor phase osmometry or gel permeation chromatography); 2) the polyol ethers (e.g., poly(oxyethylene-oxypropylene) ethers); 3) ester oils including natural and synthetic triglycerides; 4) natural oil fractions such as mineral oils and those referred to as bright stocks (including all relatively viscous products formed during conventional lubricating oil manufacture from petroleum). Thus, any oil or other material recognized by those skilled in the art as possessing lubricity characteristics may be used as a base oil for purposes of this invention.

Ashless Dispersants

Within the prior art in the realm of motor fuel are a wide range of materials regarded as ashless dispersants by those of ordinary skill in such art. There are a great 10 many materials capable of functioning in this regard, including various Mannich bases, ethyleneamines, polylakylene polyamines, and other primary, secondary and tertiary amines known in the art. The following is provided to be exemplary and not delimitive of the scope of ashless dispersants which may be employed in the context of the present invention.

A large number of such ashless dispersants are derivatives of high molecular weight carboxylic acid acylating agents. Typically, the acylating agents are prepared by reacting an olefin (e.g., a polyalkene such as polybutene) or a derivative thereof, containing for example at least about 10 aliphatic carbon atoms or generally at least 30 to 50 aliphatic carbon atoms, with an unsaturated carboxylic acid or derivative thereof such as acrylic acid, methylacrylate, maleic acid, fumaric acid and maleic anhydride. Dispersants are prepared from the high molecular weight carboxylic acid acylating agents by reaction with, for example, amines characterized by the presence within their structure of at least one N—H group, alcohols, reactive metal or reactive metal compounds, and combinations of the above. The prior art relative to the preparation of such carboxylic acid derivatives is summarized in U.S. Pat. No. 4,234,435.

It also has been suggested that the carboxylic acid derivative compositions such as those described above can be post-treated with various reagents to modify and improve the properties of the compositions. Acylated nitrogen compositions prepared by reacting the acylating reagents described above with an amine can be post-treated, for example, by contacting the acylated nitrogen compositions thus formed with one or more post-treating reagents selected from the group consisting of boron oxide, boron oxide hydrate, boron halides, boron acids, esters of boron acid, carbon disulfide, sulfur, sulfur chlorides, alkenyl cyanides, carboxylic acid acylating agents, aldehydes, ketones, phosphoric acid, epoxides, etc. Lists of the prior art relating to post-treatment of carboxylic ester and amine dispersants with reagents such as those described above are contained in a variety of patents such as U.S. Pat. No. 4,203,855 (Col. 19, lines 16–34) and U.S. Pat. No. 4,234,435 (Col. 42, lines 33–46). The use of isophthalic and terephthalic acids as corrosion-inhibitors is described in U.S. Pat. No. 2,809,160. The corrosion-inhibitors are used in combination with detergent additives.

The preparation of lubricating oils containing ashless dispersants obtained by reaction of aliphatic and aromatic polycarboxylic acids with acylated amines have been described previously. For example, U.S. Pat. No. 4,234,435 describes lubricating oils containing carboxylic acid derivative compositions prepared by post-treating acylated amines with a variety of compositions including carboxylic acid acylating agents such as terephthalic acid and maleic acid. U.S. Pat. No. 3,287,271 and French Pat. No. 1,367,939 describe detergent-corrosion inhibitors for lubricating oils prepared by combining a polyamine with a high molecular weight succinic anhydride and thereafter contacting the resulting product with an aromatic dicarboxylic acid of from 8 to 14 carbon atoms wherein the carboxyl groups are bonded to annular carbon atoms separated by at least one annular carbon atom. Illustrative of such aromatic dicarboxylic acids are isophthalic acid, terephthalic acid and various derivatives thereof. Lubricating compositions containing amine salts of a phthalic acid are described in U.S. Pat. No. 2,900,339. The amine salts are thermally unstable salts of the phthalic acid and a basic tertiary amine. U.S. Pat. No. 3,692,681 describes dispersions of phthalic acid in hydrocarbon media containing highly hindered acylated alkylene polyamines. The polyamines are prepared by reaction of an alkenyl succinic anhydride with an alkylene polyamine such as ethylene polyamine or propylene polyamine. The terephthalic acid or its derivative is dissolved in an auxiliary solvent such as a tertiary alcohol or DMSO, and a terephthalic acid solution is combined with a hydrocarbon solution containing the hindered acylated amine address detergent. The auxiliary solvent then is removed.

U.S. Pat. No. 3,216,936 describes lubricant additives which are compositions derived from the acylation of alkylene polyamines. More specifically, the compositions are obtained by reaction of an alkylene amine with an acidic mixture consisting of a hydrocarbon-substituted succinic acid having at least about 50 aliphatic carbon atoms in the hydrocarbon group and an aliphatic monocarboxylic acid, and thereafter removing the water formed by the reaction. The ratio of equivalents of said succinic acid to the mono-carboxylic acid in the acidic mixture is from about 1:0.1 to about 1:1. The aliphatic mono-carboxylic acids contemplated for use include saturated and unsaturated acids such as acetic acid, dodecanoic acid, oleic acid, naphthenic acid, formic acid, etc. Acids having 12 or more aliphatic carbon atoms, particularly stearic acid and oleic acid, are especially useful. The products described in the '936 patent also are useful in oil-fuel mixtures for two-cycle internal combustion engines.

British Pat. No. 1,162,436 describes ashless dispersants useful in lubricating compositions and fuels. The compositions are prepared by reacting certain specified alkenyl substituted succinimides or succinic amides with a hydrocarbon-substituted succinic acid or anhydride. The arithmatic mean of the chain lengths of the two hydrocarbon substituents is greater than 50 carbon atoms. Formamides of monoalkenyl succinimides are described in U.S. Pat. No. 3,185,704. The formamides are reported to be useful as additives in lubricating oils and fuels.

U.S. Pat. Nos. 3,639,242 and 3,708,522 describe compositions prepared by post-treating mono- and polycarboxylic acid esters with mono- or polycarboxylic acid acylating agents. The compositions thus obtained are reported to be useful as dispersants in lubricants and fuels.

One preferred method for preparing compositions according to the invention is to begin with a major amount of a base oil material and add the other selected ingredients to the base oil, with sufficient agitation to provide a homogeneous mixture within a reasonable time. When the viscosity of the additive is much greater than that of the base oil, it is beneficial to provide heating to the base oil to facilitate dissolution and homogeneity. This is especially true in the cases where polymeric materials are added to base oils. However, the dissolution of all of the additives used in the invention in a base oil is well known in the art and is thus within the skill level of an ordinary artisan in the oil additives field.

The compositions of the present invention may vary widely in composition depending upon the intended use of the final composition. However, those of ordinary skill in formulating lubricating oils, functional fluids, cutting oils, emulsions, etc., in which LAB based detergent materials are used as a component readily recognize that the detergents prepared from LAB materials provided by the invention may be used as direct, drop-in substitutes for many detergent components in current formulations, including those which are based on linear alkylbenzenes and those which are not. Compositions which include detergents based upon the linear alkylbenzenes of the invention offer superior detergency over formulations which contain linear alkylbenzene based detergent materials of the prior art, on a molar basis, owing to the unique isomer distribution provided by the present invention.

Another aspect of the present invention is the use of the LAB surfactants in fuel formulations on which various internal combustion engines including diesel, automobile, and jet engines may be operated. Since the LAB surfactants of this invention may be anionic in nature, such as in the cases when the detergent molecule is a sulfonate, it is possible to provide charge balance using a cation which is known to impart beneficial properties to motor fuels. Such cations may include the alkali and alkaline earth metals as the use of such are well known for the properties they impart to fuel compositions. Further, the prior art discloses many ashless dispersants useful as additives in fuels and lubricant compositions. Many of these are cationic in nature and are thus capable of providing charge balance to chemical compounds in which the anionic portion is derived from the LAB according to this invention, to provide a neutral, oil or fuel soluble material which possesses both detergent and dispersant characteristics.

One particular and surprising advantage of using the catalysts of this invention to produce alkylbenzenes having relatively high 2-phenyl isomer content is that a low content of dialkylbenzene components are found in the alkylbenzene product mixture. This is important since dialkylbenzenes are generally regarded as undesirable, and the presence of such species tends to raise the viscosity of the alkylbenzene reaction product mixture. Thus, using conventional alkylation technology known in the art, it is common for alkylbenzenes produced in accordance with prior art methods to have a viscosity greater than about 145 SUS viscosity units at a temperature of 37.8 degrees centigrade. However, alkylation of benzene with olefins in the $C_{16}$–$C_{30}$ range in accordance with this invention provides a product having an SUS viscosity of 85 at 37.8 degrees centigrade. Generally speaking, alkylbenzenes made by alkylation of benzene with olefins in the $C_{16}$–$C_{30}$ range using catalysts an procedures taught herein results in the alkylbenzenes containing less than 1% of dialkylbenzenes.

Consideration must be given to the fact that although the instant invention has been shown and described with respect to certain preferred embodiments including selection of linear alkylbenzenes from which detergents are produced, it is likely that this specification shall inspire those skilled in the lubricating arts upon its reading to make alterations and modifications to compositions according to the invention and arrive at compositions substantially equivalent in function. The scope of the present invention includes all such equivalent alterations and modifications, and is limited only by the scope of the claims appended hereto.

What is claimed is:

1. A composition useful as a lubricant that is formed from components comprising:

a) a base oil; and b) an effective detergent amount of an alkylbenzene surfactant component, said component characterized as comprising any amount between 35.00% and 82.00% by weight based upon the total weight of the component, including every hundredth percentage therebetween, of derivatives of the 2-phenyl isomers of alkylbenzenes described by the general formula:

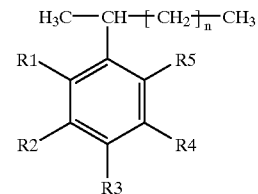

in which n may be any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, a sulfonate group, and a sulfonate ester group.

2. A composition according to claim 1 wherein $R_2$ and $R_3$ are each independently selected from the group consisting of hydrogen and a sulfonate group, $R_1$ and $R_5$ are hydrogen, and $R_4$ is selected from hydrogen, a methyl group, or an ethyl group.

3. A composition according to claim 1 wherein $R_2$ is sulfonate, $R_3$ is methyl, $R_1$ and $R_5$ are hydrogen, and $R_4$ is selected from the group consisting of: hydrogen, a methyl group, or an ethyl group.

4. A composition according to claim 1 wherein $R_2$, $R_3$, and $R_4$ are each independently selected from the group consisting of hydrogen and a sulfonate group, and $R_1$, $R_5$ are each independently selected from the group consisting of hydrogen, a methyl group, or an ethyl group.

5. A composition as in claim 1 in which $R_1$ $R_2$, and $R_5$ are hydrogen, $R_3$ is selected from the group consisting of a methyl group or an ethyl group, and $R_4$ is a sulfonic acid group.

6. A composition as in claim 1 in which $R_1$, $R_2$, and $R_4$ are hydrogen, $R_3$ is selected from the group consisting of a methyl group or an ethyl group, and $R_5$ is a sulfonic acid group.

7. A composition as in claim 1 in which $R_1$, $R_2$, and $R_4$ are hydrogen, $R_1$ is selected from the group consisting of a methyl group or an ethyl group, and $R_3$ is a sulfonic acid group.

8. A composition as in claim 1 in which $R_1$, $R_3$, and $R_4$ are hydrogen, $R_5$ is selected from the group consisting of a methyl group or an ethyl group, and $R_2$ is a sulfonic acid group.

9. A composition according to claim 1 in which $R_2$ and $R_5$ are both methyl and $R_1$, $R_3$, and $R_4$ are each independently selected from the group consisting of hydrogen or a sulfonate group.

10. A composition according to claim 1 in which $R_4$ and $R_5$ are both methyl and $R_1$, $R_2$, and $R_3$ are each independently selected from the group consisting of hydrogen or a sulfonate group.

11. A composition according to claim 1 in which $R_3$ and $R_4$ are both methyl and $R_1$, $R_2$, and $R_5$ are each independently selected from the group consisting of hydrogen or a sulfonate group.

12. A composition according to claim 1 wherein the predominant amount of said derivatives are those in which only one of $R_1$, $R_2$, $R_3$, $R_4$, and $R_5$ is a sulfonate group, and in which said derivatives are sulfonate salts of metals selected from the group consisting of: alkali metals or alkaline earth metals.

13. A composition according to claim 12 wherein said salts are salts of metals selected from the group consisting of: sodium, potassium, lithium, calcium, magnesium, strontium and barium.

14. A composition according to claim 1 further comprising a material selected from the group consisting of: corrosion-inhibiting agent, detergent, dispersant, antioxidant, viscosity improving agent, antiwear agent, extreme-pressure agent, pour-point depressant, friction-modifier, fluidity-modifier, anti-foam agent, or mixture of two or more thereof.

15. A composition according to claim 1 further comprising any amount between 0.01% and 20.00% by weight based upon the total weight of the composition of a component that comprises at least one other component known to be useful in formulating lubricants, oils, cutting fluids and the like, wherein at least one of said other components is selected from the group consisting of: anti-oxidants, friction modifiers, pour point depressants, viscosity index improvers, extreme pressure additives, sulfurized olefins, water, aromatic hydrocarbons, aliphatic hydrocarbons, anti-foam agents, a hydrocarbon-based oil, a vegetable oil, a metallic dithiophosphate, an overbased sulfonate, a dye, a hydrocarbon-soluble ashless dispersant, an alkali metal or alkaline earth metal salt of a sulfonic acid, an alkali metal or alkaline earth metal salt of a fatty acid and alkylbenzene sulfonates having a 2-phenyl isomer content of less than 50.00%.

16. A composition according to claim 1 wherein the 2-phenyl isomers content of the alkylbenzene surfactant component comprises any amount between 45.00% and 82.00% by weight based upon the total weight of the component, including every hundredth percentage therebetween.

17. A composition according to claim 1 wherein the 2-phenyl isomers content of the alkylbenzene surfactant component comprises any amount between 57.00% and 82.00% by weight based upon the total weight of the component, including every hundredth percentage therebetween.

18. A composition according to claim 1 wherein said alkylbenzene surfactant component is present in any amount between 0.03% and 49.95% by weight based upon the total weight of said composition useful as a lubricant.

19. A composition as in claim 1 wherein the alkylbenzene surfactant component comprises only one alkyl group bonded to a benzene ring, and wherein none of $R_1$, $R_2$, $R_3$, $R_4$, or $R_5$ are hydrocarbyl.

20. A composition as in claim 19 wherein the alkyl group is substantially linear.

21. A composition as in claim 19 wherein the alkyl group is a branched alkyl group.

22. A composition according to claim 14 wherein said material is present in any amount between 0.10% and 25.00% by weight based upon the total weight of said composition useful as a lubricant.

23. A composition according to claim 14 wherein said material is a mixture of branched alkylbenzene sulfonates wherein said branched alkylbenzene sulfonates comprise one branched alkyl group bonded to a benzene ring, and wherein said alkyl group comprises any integral number of carbon atoms between 16 and 30.

24. A composition useful as a lubricant that is formed from components comprising:
a) an alkylbenzene surfactant component present in any amount between 0.01% and 50.0% by weight based upon the total weight of the composition, said component characterized as comprising any amount between 37.00% and 82.00% by weight based upon the total weight of the component, including every hundredth percentage therebetween, of derivatives of the 2-phenyl isomers of alkylbenzenes described by the general formula:

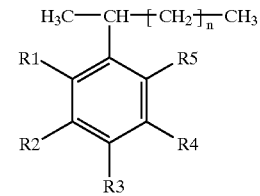

wherein n is equal to any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, a sulfonate group, and a sulfonate ester group; and
b) at least 50.0% by weight of a base oil.

25. A composition useful as a fuel for an internal combustion engine that is formed from components comprising:

a) a motor fuel; and
b) an effective detergent amount of an alkylbenzene surfactant component, said component characterized as comprising any amount between 35.00% and 82.00% by weight based upon the total weight of the component, including every hundredth percentage therebetween, of derivatives of the 2-phenyl isomers of alkylbenzenes described by the general formula:

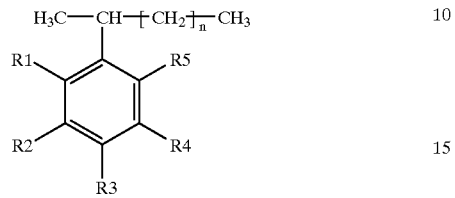

wherein n is equal to any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, a sulfonate group, and a sulfonate ester group.

26. A composition according to claim 25 further comprising a base oil present in an amount sufficient to effect lubrication of fuel injectors.

27. A composition according to claim 25 in which said derivatives are sulfonate salts of metals selected from the group consisting of: alkali metals or alkaline earth metals, and wherein at least 51% by weight of said derivatives are those in which only one of $R_1$, $R_2$, $R_3$, $R_4$, and $R_5$ is a sulfonate group.

28. A composition according to claim 27 wherein said salts include are selected from the group of: sodium, potassium, lithium, calcium, magnesium, strontium, barium, and ammonium salts.

29. A composition according to claim 28 wherein the derivatives are ammonium salts and said ammonium salts include at least one ammonium salt capable of functioning as an ashless dispersant in a fuel composition useful in internal combustion engines.

30. A composition of matter that comprises:
a) a cationic portion comprising a hydrocarbon soluble ashless dispersant; and
b) an anionic portion comprising an alkylbenzene sulfonate surfactant component, said alkylbenzene sulfonate surfactant component characterized as comprising any amount between 35.00% and 82.00% by weight based upon the total weight of the alkylbenzene sulfonate surfactant component, including every hundredth percentage therebetween, of sulfonates of the 2-phenyl isomers of alkylbenzenes described by the general formula:

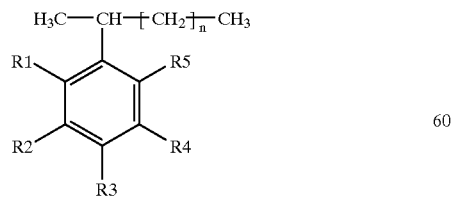

wherein n is equal to any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, or a sulfonate group, or a sulfonate ester group, with the proviso that only one of $R_1$, $R_2$, $R_3$, $R_4$, and $R_5$ is a sulfonate group.

31. A composition of matter comprising:
a) a minor amount of a composition according to claim 30; and
b) a major amount of a material selected from the group consisting of: a motor fuel, hydrocarbon diluent, or a base oil.

32. A concentrate which comprises:
a) an alkylbenzene surfactant component, said component characterized as comprising any amount between 35.00% and 82.00 % by weight based upon the total weight of the component, including every hundredth percentage therebetween, of derivatives of the 2-phenyl isomers of alkylbenzenes described by the general formula:

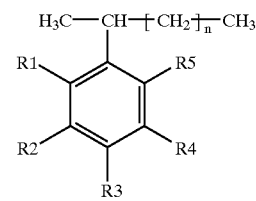

wherein n is equal to any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, a sulfonate group, and a sulfonate ester group; and
b) a hydrocarbon diluent.

33. A composition of matter according to claim 32 further comprising a base oil.

34. An mixture from which surfactants, lubricants, and motor fuels may be produced, said mixture characterized as comprising any amount between 35.00% and 82.00% by weight based upon its total weight, including every hundredth percentage therebetween, of the 2-phenyl isomers of alkylbenzenes described by the general formula:

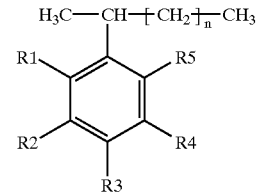

in which n is equal to any integer between 13 and 27, and in which $R_1$, $R_2$, $R_3$, $R_4$, and $R_5$ are each independently selected from the group consisting of: hydrogen, a methyl group, an ethyl group, a propyl group, a butyl group, a sulfonic acid group, a sulfonate group, and a sulfonic ester group, wherein the dialkylbenzene content of the mixture is less than 1.0%, and wherein the viscosity of the alkylbenzene mixture is less than 140 SUS units@ 37.8 degrees centigrade.

35. A mixture according to claim 34 wherein the viscosity of the mixture is less than 120 SUS units@37.8 degrees centigrade.

36. A mixture according to claim 34 wherein the viscosity of the alkylbenzene mixture is less than 100 SUS units@37.8 degrees centigrade.

37. A mixture according to claim 34, wherein said derivatives include a sulfonic ester group appended to the benzene ring.

38. A mixture according to claim 37 wherein the alcohol portion of the ester from which said sulfonic ester group is derived comprises a $C_1$ to $C_{25}$ hydrocarbon chain, whether linear alkyl or branched alkyl.

39. The process of providing a metal surface with a lubricating film comprising the step of contacting a composition according to claim 1 to said metal surface.

40. The process of operating an internal combustion engine which comprises the step of introducing a composition according to claim 25 into a combustion chamber and igniting the fuel.

* * * * *